(12) United States Patent
Giphart et al.

(10) Patent No.: US 12,016,725 B2
(45) Date of Patent: Jun. 25, 2024

(54) ULTRASOUND EYE SCANNING DEVICE

(71) Applicant: ArcScan, Inc., Golden, CO (US)

(72) Inventors: Johan E. Giphart, Aurora, CO (US); Andrew K. Levien, Morrison, CO (US); Tom Wilmering, Eldorado Springs, CO (US); Barry Schafer, Folsum, CA (US); John D. Watson, Evergreen, CO (US)

(73) Assignee: ArcScan, Inc., Golden, CO (US)

( * ) Notice: Subject to any disclaimer, the term of this patent is extended or adjusted under 35 U.S.C. 154(b) by 76 days.

(21) Appl. No.: 17/411,570

(22) Filed: Aug. 25, 2021

(65) Prior Publication Data

US 2022/0061801 A1 Mar. 3, 2022

Related U.S. Application Data

(60) Provisional application No. 63/070,111, filed on Aug. 25, 2020.

(51) Int. Cl.
*A61B 8/10* (2006.01)
*A61B 3/00* (2006.01)
*A61B 8/00* (2006.01)

(52) U.S. Cl.
CPC ............ *A61B 8/10* (2013.01); *A61B 3/0091* (2013.01); *A61B 8/4461* (2013.01)

(58) Field of Classification Search
CPC ....... A61B 3/0091; A61B 8/10; A61B 8/4281; A61B 8/4461
See application file for complete search history.

(56) References Cited

U.S. PATENT DOCUMENTS

| | | |
|---|---|---|
| 4,245,250 A | 1/1981 | Tiemann |
| 4,817,432 A | 4/1989 | Wallace et al. |
| 5,029,587 A | 7/1991 | Baba et al. |
| 5,293,871 A | 3/1994 | Reinstein et al. |
| 5,331,962 A | 7/1994 | Coleman et al. |
| 5,776,068 A | 7/1998 | Silverman et al. |
| 6,315,727 B1 | 11/2001 | Coleman et al. |
| 6,491,637 B2 | 12/2002 | Foster et al. |
| 6,887,203 B2 | 5/2005 | Phillips et al. |
| 7,048,690 B2 | 5/2006 | Coleman et al. |
| D601,698 S | 10/2009 | Stephenson et al. |
| 8,317,702 B2 | 11/2012 | Yu et al. |
| 8,317,709 B2 | 11/2012 | Eilers et al. |
| 8,496,588 B2 | 7/2013 | Eilers et al. |
| 8,510,883 B2 | 8/2013 | Eilers et al. |

(Continued)

OTHER PUBLICATIONS

U.S. Appl. No. 63/023,661, filed May 12, 2021, Reinstein et al.
Pavlin et al., "Ultrasound Biomicroscopy in Plateau Iris Syndrome," American Journal of Ophthalmology, Apr. 1992, vol. 113, pp. 390-395.
Atchison et al., "Optics of the Human Eye," Butterworth-Heinemann, First Edition, Feb. 29, 2000, Edinburgh, ISBN 0 7506 3775 7, abstract only, 3 pages.

(Continued)

*Primary Examiner* — Mark D Remaly
(74) *Attorney, Agent, or Firm* — Sheridan Ross P.C.

(57) ABSTRACT

The present disclosure is directed to an apparatus for an improved ultrasound eye scanning device wherein the size of the scan head is reduced significantly and the entire instrument can be placed on a desktop. The improved ultrasound eye scanning device also utilizes imaging goggles to enable better coupling between the patient and the instrument. The imaging goggles also allow both eyes of the patient to be scanned without the patient moving. Another innovation of the ultrasound imaging system according to the present disclosure is the use of the contralateral (opposite) eye for fixation and focusing during scanning.

20 Claims, 17 Drawing Sheets

(56) References Cited

U.S. PATENT DOCUMENTS

| | | |
|---|---|---|
| 8,758,252 B2 | 6/2014 | Eilers et al. |
| 9,149,254 B2 | 10/2015 | Watson |
| 9,320,427 B2 | 4/2016 | Levien et al. |
| 9,597,059 B2 | 3/2017 | Watson et al. |
| 10,531,859 B2 | 1/2020 | Watson et al. |
| 2009/0153796 A1 | 6/2009 | Rabner |
| 2010/0004538 A1 | 1/2010 | Eilers et al. |
| 2013/0237826 A1 | 9/2013 | Levien |
| 2014/0049752 A1 | 2/2014 | Eilers et al. |
| 2014/0249422 A1 | 9/2014 | Eilers et al. |
| 2015/0238166 A1 | 8/2015 | Heath et al. |
| 2016/0166235 A1 | 6/2016 | Levien et al. |
| 2017/0119345 A1 | 5/2017 | Levien et al. |
| 2018/0279870 A1 | 10/2018 | Walsh et al. |
| 2019/0290939 A1 | 9/2019 | Watson et al. |
| 2020/0015789 A1 | 1/2020 | Johnson |
| 2021/0186458 A1 | 6/2021 | Giphart et al. |
| 2021/0204906 A1 | 7/2021 | Giphart et al. |
| 2021/0353252 A1 | 11/2021 | Reinstein et al. |
| 2021/0401401 A1 | 12/2021 | Gilphart et al. |

OTHER PUBLICATIONS

Coleman et al., "Ultrasonography of the Eye and Orbit," Lippincott Williams & Wilkins, Second Edition, 2006, 205 pages, uploaded in 3 parts.

Rozema et al., "Methods to Estimate the Size and Shape of the Unaccommodated Crystalline Lens In Vivo," Visual Psychophysics and Physiological Optics, Investigative Ophthalmology & Visual Science, May 2012, vol. 53(6), pp. 2533-2540.

Hernandez et al., "Calculation of crystalline lens power using a modification of the Bennett method," Optical Society of America, Oct. 21, 2015, OSA Nov. 1, 2015 vol. 6(11), 15 pages.

Bennett, "A method of determining the equivalent powers of the eye and its crystalline lens without resort to phakometry," Ophthalmic Physiol. Opt. 1988, vol. 8(1), pp. 53-59, abstract only, 1 page.

Olsen, "On the calculation of power from curvature of the cornea," British Journal of Ophthalmology, 1986, vol. 70, pp. 152-154.

International Search Report and Written Opinion for International (PCT) Patent Application No. PCT/US2021/047510, dated Feb. 16, 2022 15 pages.

International Preliminary Report on Patentability for International (PCT) Patent Application No. PCT/US2021/047510, dated Mar. 9, 2023 10 pages.

ULTRASOUND EYE SCANNING DEVICE

CROSS-REFERENCE TO RELATED APPLICATIONS

This application claims the benefits, under 35 U.S.C. § 119(e), of U.S. Provisional Application Ser. No. 63/070,111 entitled "An Improved Ultrasound Eye Scanning Device" filed Aug. 25, 2020, which is incorporated herein by reference.

FIELD

The present disclosure relates to an improved ultrasound eye scanning device wherein the size of the scan head is reduced significantly and the entire instrument can be placed on a desktop.

BACKGROUND

Ultrasonic imaging has found use in accurate and reproducible measurements of structures of the eye, such as, for example, the cornea and lens capsule. Such measurements provide an ophthalmic surgeon valuable information that can be used to guide various surgical procedures, such as LASIK and lens replacement, for correcting refractive errors. They also provide diagnostic information after surgery has been performed to assess the geometrical location of corneal features such as the LASIK scar and lens features such as lens connection, position and orientation. This allows the surgeon to assess post surgical changes in the cornea or lens and to take steps to correct any problems that develop. Ultrasonic imaging can also provide insights valuable for the diagnosis and treatment of glaucoma.

Except for on-axis measurements, dimensions and locations of eye components behind the iris cannot be fully determined by optical means. Ultrasonic imaging in the frequency range of about 5 MHz to about 80 MHz can be applied to make accurate and precise measurements of structures of the eye, such as the cornea, lens capsule, ciliary muscle, zonules and the like.

An arc scanner is an ultrasound scanning device utilizing a transducer that both sends and receives ultrasound pulses as it moves along an arcuate guide track. The arcuate guide track has a center of curvature whose position can be moved to scan different curved surfaces. Later versions of arc scanners have mechanisms that allow the radius of curvature of the scanner to be changed. In this type of scanner, a transducer is moved along an arcuate guide track whose center of curvature can be changed and set approximately at the center of curvature of the eye surface of interest. The transducer generates many acoustic pulses as it moves along the arcuate guide track. These pulses reflect off specular surfaces and other tissue interfaces within the eye. Each individual return pulse is detected and digitized to produce a series of A-scans. The A-scans can then be combined to form a cross-sectional image called a B scan of the eye features of interest.

At a center frequency of about 38 MHz, a typical arc scanner has an axial resolution of about 25 microns and a lateral resolution of about 60 microns. The reproducibility of arc scanner images is typically about 2 microns.

Ultrasonic imaging requires a liquid medium to be interposed between the eye being imaged and the transducer, which requires, in turn, that the eye, the transducer and the path between them be at all times immersed in a liquid medium. Concern for safety of the cornea introduces the practical requirement that the liquid medium be either pure water or normal saline water solution. There are reasons to prefer that the medium be pure water or physiologic saline (also known as normal saline) but the embodiments do not exclude other media suitable for conducting acoustic energy in the form of ultrasound. Most other media present an increased danger to the patient's eye, even with a barrier interposed between the eye and the ultrasonic transducer. Barriers can leak or be breached, allowing the liquids on either side to mix, thus bringing a potentially harmful material into contact with the eye.

An eyepiece or in the case of the present disclosure, imaging goggles, serve to complete a continuous acoustic path for ultrasonic scanning, that path extending from the transducer to the surface of the patient's eye. The eyepiece also separates the water in which the patient's eye is immersed from the water in the chamber in which the ultrasound transducer and guide track assembly are contained. Finally, the eyepiece provides a steady rest for the patient and helps the patient to remain steady during a scan. To be practical, the eyepiece should be free from frequent leakage problems, should be comfortable to the patient and its manufacturing cost should be low since it should be replaced for every new patient.

Another ultrasound scanning method is known as Ultrasound Bio Microscopy as embodied in a hand-held device commonly known as a UBM. A UBM can capture anterior segment images using a transducer to emit short acoustic pulses ranging from about 20 to about 80 MHz. This type of ultrasound scanner is also called a sector scanner.

A UBM is a hand-held ultrasonic scanner whose beams sweep a sector like a radar transmitter. The swept area is pie-shaped with its central point typically located near the face of the ultrasound transducer. In this type of scanner, an ultrasonic transducer oscillates about a fixed position so as to produce many acoustic echoes which are captured as a series of A-scans. These A-scans can then be combined to form a B-scan of a localized region of interest within the eye.

The UBM method is capable of making qualitative ultrasound images of the anterior segment of the eye but cannot make accurate, precision, comprehensive, repeatable images of the cornea, lens or other components of the eye required for glaucoma screening, keratoconus evaluation or lens sizing. This is because of two reasons. First, the UBM is a hand-held device and relies on the steadiness of the operator's hand to maintain a fixed position relative to the eye being scanned for several seconds. Second, the UBM is pressed firmly onto the patient's eye to make contact with the patient's cornea to obtain good acoustic coupling. This gives rise to some distortion of the cornea and the eyeball.

Between these two limitations, the resolution is limited, at best, to the range of about 40 to 60 microns and the reproducibility, at best, can be no better than about 20 microns.

Optical Coherence Tomography (OCT) is a light-based imaging technology that can image the cornea though not to the full lateral extent as an ultrasound instrument. OCT cannot see behind the scleral wall or the iris and is therefore of limited use in glaucoma screening. OCT does well for imaging the central retina though only to the lateral extent allowed by a dilated pupil. OCT images of the retina can disclose the damage caused by glaucoma. The approach of a precision ultrasound scanning device is to detect the onset of glaucoma by imaging structural changes in the anterior segment before any retinal damage occurs so that the disease can be identified and successfully treated with drugs and/or stents.

Ultrasonic imaging has been used in corneal procedures such as LASIK to make accurate and precise images and maps of cornea thickness which include epithelial thickness, Bowman's layer thickness and images of LASIK flaps.

New procedures such as implantation of accommodative lenses may provide nearly perfect vision without spectacles or contact lenses. Implantation of accommodative lenses requires precision measurements of, for example, the position and width of the natural lens for successful lens powering and implantation. Ultrasonic imaging can be used to provide the required accurate images of the natural lens especially where the zonules attach the lens to the ciliary body which is well off-axis and behind the iris and therefore not accessible to optical imaging.

Recent advances in ultrasonic imaging have allowed images of substantially the entire lens capsule to be made. This has opened up the ability of diagnostic devices to assist in both research of lens implantation devices and strategies, and to planning, executing and follow-up diagnostics for corrective lens surgery including specialty procedures such as glaucoma and cataract treatments as well as implantation of clear intraocular lenses including accommodative lens.

A phakic intraocular lens (PIOL) is a special kind of intraocular lens that is implanted surgically into the eye to correct myopia. It is called "phakic" (meaning "having a lens") because the eye's natural lens is left untouched. Intraocular lenses that are implanted into eyes after the eye's natural lens has been removed during cataract surgery are known as pseudophakic. Phakic intraocular lenses are considered for patients with high refractive errors when laser options, such as LASIK and PRK are not the best surgical options.

PIOLs made of collamer (a foldable gel-like substance) require a very small incision due the flexibility of the material. In the cases where refractive outcomes are not the best, LASIK can be used for fine-tuning. If a patient eventually develops a visually significant cataract, the PIOLs can be removed (explanted) when the patient undergoes cataract surgery.

Speed of Sound in Different Regions of an Eye

Both ultrasound sector and ultrasound arc scanning instruments record time-of-arrival of reflected ultrasound pulses. A speed of sound of the medium is then used to convert these time of arrival measurements to distance measurements. Traditionally, a single representative speed of sound value is used. Usually the speed of sound of water at 37 C (1,531 m/s) is used although speeds of sound from 1,531 m/s to 1,641 m/s may be used (1,641 m/s is the speed of sound in a natural human lens).

The speed of sound varies in the different anterior segment regions of the eye such as the cornea, aqueous, natural lens and vitreous fluid. The speed of sound in these different regions have been measured by various researchers and are reasonably known. Therefore if the interfaces of these regions can be identified, the appropriate speeds of sounds for these regions can be used to convert times of arrivals to distances with more accuracy. A method for accomplishing this is described in U.S. Pat. No. 9,149,254 which is incorporated herein by reference.

Unintended Eye Motion and Instrument Motion During Scanning

It is also important to compensate for unintended patient head or eye motion because a scan of the anterior segment scan or lens capsule scan is typically made by overlaying two or three separate scans (such as an arcuate scan followed by two linear scans, also described in U.S. Pat. No. 9,597,059 entitled "Tracking Unintended Eye Movements in an Ultrasonic Scan of the Eye").

Unintended patient eye motion includes saccades which are quick, simultaneous rotations of both eyes in the same direction involving a succession of discontinuous individual rotations of the globe of the eye in the eye socket.

The speed of transducer motion in an precision scanning device such as described, for example, in U.S. Pat. No. 8,317,709, is limited because its movement is in a bath of water and excessive speed of motion of the transducer and its carriage can result in vibration of the entire instrument. In practice, a set of ultrasound scans can be carried out in about 1 to about 3 minutes from the time the patient's eye is immersed in water to the time the water is drained from the eyepiece.

The actual scanning process itself can be carried out in several tens of seconds, after the operator or automated software completes the process of centering and range finding. As is often the case, the patient may move his or her head slightly or may move his or her eye globe in its socket during this time. In some cases, the patient's heartbeat can be detected as a slight blurring of the images. If patient movements are large, the scan set can always be repeated.

Creating Composite B-Scans

The arc scanning instrument of the present disclosure can create several distinct scan types. These are:
- an arcuate scan having a fixed radius of curvature
- a linear scan
- a combined arcuate and linear scan allowing for various radii of curvature including inverse radii of curvature These scans can be combined to form composite images because each image is formed from very accurate time-of-arrival data and transducer positional data. However, combining these separate scans into a composite scan must take into account patient eye movement during scanning; and instrument movement during scanning.

Due to the need for an eye seal to provide a continuous medium for the ultrasound signal to travel between the transducer and the anterior surface of the cornea of the patient's eye, any scanning device has a limitation in the range of movement the transducer can make relative to the eye. The range of the scanning device can be expanded to cover more of the anterior segment by introducing intentional and controlled eye movements and scanning the newly exposed portion of the eye that can now be reached. Registration techniques can be used to combine the scans of different eye positions to create a more complete composite image of the anterior segment of the eye.

U.S. patent application Ser. No. 16/422,182 entitled "Method for Measuring Behind the Iris after Locating the Scleral Spur" is published as US 20200015789. This application is directed towards a method for locating the scleral spur in an eye using a precision ultrasound scanning device for imaging of the anterior segment of the eye. One of the applications of a precision ultrasound scanning device or instrument is to image the region of the eye where the cornea, iris, sclera and ciliary muscle are all in close proximity. By using a knowledge of the structure of the eye in this region and employing binary filtering techniques, the position of the scleral spur can be determined. Once the position of the scleral spur is determined, a number of measurements that characterize the normal and abnormal shapes of components within this region of the anterior segment of the eye can be made. Many of the ideas disclosed in this application may be used to form accurate composite images.

A Remaining Problem

An ultrasonic scan of the eye may include one or more rapid B-scans (each B-scan formed from a plurality of A-scans) at each of several meridians (typically about 3 to about 12 meridians) and these may be combined automatically to form a comprehensive image of the anterior segment. Therefore it is necessary to rapidly scan a patient to reduce the possibility of patient eye motion during a scan session. Further, it may be necessary to re-scan a patient at a later time in order to determine if changes in features or dimensions has occurred.

It is also important to compensate for unintended patient head or eye motion because a scan of the anterior segment scan or lens capsule scan is typically made by overlaying two or three separate scans (such as an arcuate scan followed by two linear scans, also described in U.S. Pat. No. 9,597,059 entitled "Tracking Unintended Eye Movements in an Ultrasonic Scan of the Eye".

The speed of transducer motion in a precision scanning device such as described, for example, in U.S. Pat. No. 8,317,709, is limited because its movement is in a bath of water and excessive speed of motion of the transducer and its carriage can result in vibration of the entire instrument. In practice, a set of ultrasound scans can be carried out in about 1 to about 3 minutes from the time the patient's eye is immersed in water to the time the water is drained from the eyepiece. The actual scanning process itself can be carried out in several tens of seconds, after the operator or automated software completes the process of centering and range finding. As is often the case, the patient may move his or her head slightly or may move his or her eye in its socket during this time. In some cases, the patient's heartbeat can be detected as a slight blurring of the images. If patient movements are large, the scan set can always be repeated.

There remains, therefore, a need for a smaller ultrasound scanning device to reduce scan times without reducing capability. There also remains a need for a desktop ultrasound imaging device for ophthalmology which can be easily worked into a clinical setting. Such a device must be small and light enough to be portable and advanced enough to be able to scan both eyes at one sitting while compensating for patient eye variability, unintended eye motion and for acoustic and optical transmission variances from the various fluids in the imaging transmission path.

SUMMARY

These and other needs are addressed by the present disclosure. The various embodiments and configurations of the present disclosure are directed generally to ultrasonic imaging of biological materials of an eye, such as the cornea, lens capsule, ciliary muscle, zonules and the like, and in particular directed to an improved ultrasound eye scanning device wherein the size of the scan head is reduced significantly and the entire instrument can be placed on a desktop.

Some of the features embodied in an ultrasound imaging system according to the present disclosure include:

a substantial reduction in size and weight of the positioning and scan head mechanisms over those of the Insight 100™. The proposed positioning and scan head mechanisms are approximately one third the size of those of the Insight 100™ with no loss of functionality.

because the size has been reduced and the arc angle through which the transducer can be moved is preserved or even increased somewhat, the time it takes to do an arcuate sweep, or a combined arcuate linear sweep, is reduced.

the ultrasound imaging system of the present disclosure is now a desktop instrument. It is similar in size and weight to other ophthalmic imaging instruments such as the IOL Master and Optivue and Topcon OCT systems.

the control and image processing computer is on a board now situated within the electronics section which, in turn, is internal to the instrument.

wider angle coverage with sector scanner type mechanism as alternative to a more compact prior art arc scanning scan head mechanism.

the monitor is now decoupled from the instrument and can be a stand-alone monitor, a tablet or a phone, all of which can communicate to the on-board computer via short range wireless.

a saline bag can be placed in a compartment inside the instrument where the saline solution can be warmed to body temperature.

the linear and arcuate track mechanisms can move on either fluid bearings such as used on the Insight 100™ or solid-surface bearing plates made from materials such as Teflon.

bilateral imaging goggles replace the Insight 100™ eye piece—the imaging goggles are constructed using similar materials and assembly techniques used in the eye piece design of the Insight 100™. The imaging goggles give better acoustical and optical coupling between the patient and the instrument and can allow both eyes of the patient to be scanned without having to remove the patient from the scanner between scanning of each eye. The system may have two scan heads or alternatively a single scan head which may be switched from side to side to scan both eyes.

the user interface is improved and can display more control and imaging information than the interface developed for the Insight 100™.

the distilled water in the instrument can be treated for biological contaminants using ultraviolet light in a location where the where the water flows through.

the use of the contralateral (opposite) eye not being scanned for fixation and possibly focusing while the other eye is being scanned. Basically, the eye to be scanned is in the dark (so it sees no flashing when the scan head moves in front of the fixation light to reduce dilation/constriction) while the opposite eye is used to look at a fixation light and possibly even a small screen to allow for focusing.

the chin rest is adjustable. There are small buttons on the side of the device for the patient to adjust the chin rest.

An ultrasound imaging system is disclosed comprising a scan head having an arcuate guide track and a carriage movable along the guide track; imaging goggles configured to maintain the eyes of the patient in a fixed location relative to the arcuate guide track; and an ultrasound transducer operatively connected to the carriage, wherein ultrasound pulses are emitted into the eye of the patient to generate an image of an ocular structure in the eye wherein the imaging goggles and ultrasound transducer are positioned relative to each other such that, at a plurality of positions of the carriage along the arcuate guide track, a focal plane of the ultrasound transducer is positioned within the anterior segment of the eye.

The ultrasound imaging system can include an aspect wherein the focal plane of the ultrasound transducer is positioned in a cornea of the eye as the carriage moves along at least most of the arcuate guide track; wherein the focal plane of the ultrasound transducer is positioned in an anterior segment of the eye as the carriage moves along at least most of the arcuate guide track; wherein the focal plane of the ultrasound transducer is positioned in a lens of the eye as the carriage moves along at least most of the arcuate guide track; wherein the focal plane of the ultrasound transducer is positioned in a cornea of the eye as the carriage moves along at least about 75% of the arcuate guide track; wherein the focal plane of the ultrasound transducer is positioned in an anterior or posterior chamber of the eye as the carriage moves along at least about 75% of the arcuate guide track; wherein the focal plane of the ultrasound transducer is positioned in a lens of the eye as the carriage moves along at least about 75% of the arcuate guide track; wherein a center of curvature of the arcuate guide track is positioned between the posterior surface of the lens and the retina of the eye of the patient; and wherein in a first operating mode in which a first eye of the patient is imaged by the ultrasound imaging system, a fixation light is viewable by a second eye of the patient, but not the first eye, during imaging; and in a different second operating mode in which the second eye of the patient is imaged by the ultrasound imaging system, the fixation light is viewable by the first eye, but not the second eye, during imaging.

An ultrasound imaging system is disclosed comprising a scan head having an arcuate guide track and a carriage movable along the guide track; imaging goggles configured to maintain the eye of the patient in a fixed location relative to the arcuate guide track; an ultrasound transducer operatively connected to the carriage, wherein ultrasound pulses are emitted into the eye of the patient to generate an image of an ocular structure in the eye, and a fixation light, wherein in a first operating mode in which a first eye of the patient is imaged by the ultrasound imaging system, the fixation light is viewable by a second eye of the patient, but not the first eye during imaging; and in a different second operating mode in which the second eye of the patient is imaged by the ultrasound imaging system, the fixation light is viewable by the first eye, but not the second eye, of the patient during imaging.

The ultrasound imaging system can include an aspect wherein, in the first operating mode, a visual field of the first eye is maintained in darkness and, in the second operating mode, the visual field of the second eye is maintained in darkness; wherein, in the first and second operating modes, the imaging system provides no viewable object to the visual field of the eye being imaged; wherein the imaging goggles comprises one of a ridge and slot that is received by the other of the one of the ridge and slot of the instrument; wherein the imaging goggles and ultrasound transducer are positioned relative to each other such that, at a plurality of positions of the carriage along the arcuate guide track, a focal plane of the ultrasound transducer is positioned outside of an anterior segment of the eye; wherein the focal plane of the ultrasound transducer is positioned in a lens of the eye as the carriage moves along at least most of the arcuate guide track; wherein the focal plane of the ultrasound transducer is positioned in a cornea of the eye as the carriage moves along at least most of the arcuate guide track; wherein a focal point of the ultrasound transducer is positioned in a lens of the eye as the carriage moves along at least about 75% of a length of the arcuate guide track; wherein a focal point of the ultrasound transducer is positioned in a cornea of the eye as the carriage moves along at least about 75% of a length of the arcuate guide track; and wherein a center of curvature of the arcuate guide track is positioned between the posterior surface of the lens and the retina of the eye of the patient the eye of the patient.

A method is disclosed comprising emitting ultrasound pulses while an ultrasonic transducer moves along an arcuate guide track; receiving ultrasound pulses reflected from an optical structure of an eye of a patient; and generating an image of the ocular structure, wherein during movement along at least most of a length of the arcuate track, a focal plane of the ultrasound transducer is positioned outside of an anterior chamber of the eye.

The ultrasound imaging system can include an aspect wherein the focal plane of the ultrasound transducer is positioned in a lens of the eye as the carriage moves along at least most of the arcuate guide track; wherein the focal plane of the ultrasound transducer is positioned in a cornea of the eye as the carriage moves along at least most of the arcuate guide track; wherein the focal plane of the ultrasound transducer is positioned in an anterior or posterior chamber of the eye as the carriage moves along at least most of the arcuate guide track; wherein a focal point of the ultrasound transducer is positioned in a lens of the eye as the carriage moves along at least about 75% of a length of the arcuate guide track; wherein a focal point of the ultrasound transducer is positioned in a cornea of the eye as the carriage moves along at least about 75% of a length of the arcuate guide track; and wherein the focal plane of the ultrasound transducer is positioned in an anterior or posterior chamber of the eye as the carriage moves along at least about 75% of the arcuate guide track.

A method is disclosed comprising imaging, by an ultrasound transducer of an ultrasound imaging system, an ocular structure of a first eye of a patient, wherein a fixation light is viewable by a second eye of the patient, but not the first eye during imaging; and imaging, by the ultrasound transducer, the ocular structure of the second eye of the patient, wherein the fixation light is viewable by the first eye, but not the second eye, of the patient during imaging.

The ultrasound imaging system can include an aspect wherein, while imaging the ocular structure of the first eye, a visual field of the first eye is maintained in darkness and, while imaging the ocular structure of the second eye, the visual field of the second eye is maintained in darkness; and wherein no viewable object is provided in the visual field of the eye being imaged.

An ultrasound imaging system comprising: scan head having an arcuate guide track and a carriage movable along the guide track; imaging goggles configured to maintain the eyes of the patient in a fixed location relative to the arcuate guide track; and an ultrasound transducer operatively connected to the carriage, wherein ultrasound pulses are emitted into the eye of the patient to generate an image of an ocular structure in the eye; wherein a radius of curvature of the arcuate guide track is less than about 50 mm.

The ultrasound imaging system can include an aspect wherein the radius of curvature of the arcuate guide track is no more than about 40 mm, wherein the imaging goggles and ultrasound transducer are positioned relative to each other such that, at a plurality of positions of the carriage along the arcuate guide track, a focal plane of the ultrasound transducer is positioned within the anterior segment of the eye; wherein the radius of curvature of the arcuate guide track is no more than about 35 mm, wherein the imaging goggles and ultrasound transducer are positioned relative to each other such that, at a plurality of positions of the carriage along the arcuate guide track, a focal plane of the ultrasound transducer is positioned in a cornea of the eye; wherein the radius of curvature of the arcuate guide track ranges from about 30 to about 50 mm, wherein the imaging goggles and ultrasound transducer are positioned relative to each other such that, at a plurality of positions of the carriage along the arcuate guide track, a focal plane of the ultrasound transducer is positioned in a cornea of the eye as the carriage moves along at least most of the arcuate guide track, a focal plane of the ultrasound transducer is positioned in a lens of the eye; wherein the radius of curvature of the arcuate guide track is at least about 25 mm, wherein the imaging goggles and ultrasound transducer are positioned relative to each other such that, at a plurality of positions of the carriage along the arcuate guide track, a focal plane of the ultrasound transducer is positioned in an anterior or posterior chamber of the eye, and wherein the focal plane of the ultrasound transducer is positioned in a cornea of the eye as the carriage moves along at least about 75% of the arcuate guide track; wherein the radius of curvature of the arcuate guide track is no more than about 50 mm, wherein the imaging goggles and ultrasound transducer are positioned relative to each other such that a focal plane of the ultrasound transducer is positioned in an anterior or posterior chamber of the eye as the carriage moves along at least about 75% of the arcuate guide track; wherein the radius of curvature of the arcuate guide track is no more than about 50 mm, wherein the imaging goggles and ultrasound transducer are positioned relative to each other such that a focal plane of the ultrasound transducer is positioned in a lens of the eye as the carriage moves along at least about 75% of the arcuate guide track and; wherein a center of curvature of the arcuate guide track is positioned behind the lens of the patient and further comprising: an enclosure positioned on a support surface, the enclosure having an interior volume filled with a first fluid; a window portion positioned on a side wall of the enclosure, wherein the window portion is substantially perpendicular to the support surface wherein the window portion is substantially acoustically and optically transparent, and wherein a border of the window portion is designed to accept the imaging goggles, wherein the ultrasound transducer is positioned in the first fluid in the interior volume of the enclosure, the arcuate track being interconnected to a linear track, wherein the ultrasound transducer is configured to record a plurality of A-scan images; and a computer to combine the plurality of A-scan images to form a B-scan image, the image of the ocular structure in the eye comprising the B-scan image; and wherein: in a first operating mode in which a first eye of the patient is imaged by the ultrasound imaging system, a fixation light is viewable by a second eye of the patient, but not the first eye, during imaging; and in a different second operating mode in which the second eye of the patient is imaged by the ultrasound imaging system, the fixation light is viewable by the first eye, but not the second eye, during imaging.

An ultrasound imaging system is disclosed comprising a scan head having an arcuate guide track and a carriage movable along the guide track; imaging goggles configured to maintain the eye of the patient in a fixed location relative to the arcuate guide track; an ultrasound transducer operatively connected to the carriage, wherein ultrasound pulses are emitted into the eye of the patient to generate an image of an ocular structure in the eye, and a fixation light, wherein in a first operating mode in which a first eye of the patient is imaged by the ultrasound imaging system, the fixation light is viewable by a second eye of the patient, but not the first eye during imaging; and in a different second operating mode in which the second eye of the patient is imaged by the ultrasound imaging system, the fixation light is viewable by the first eye, but not the second eye, of the patient during imaging.

The ultrasound imaging system can include an aspect wherein, in the first operating mode, a visual field of the first eye is maintained in darkness and, in the second operating mode, the visual field of the second eye is maintained in darkness; wherein, in the first and second operating modes, the imaging system provides no viewable object to the visual field of the eye being imaged; wherein the imaging goggles comprises one of a ridge and slot that is received by the other of the one of the ridge and slot of the instrument; wherein a radius of curvature of the arcuate guide track is less than about 100 mm, wherein the imaging goggles and ultrasound transducer are positioned relative to each other such that, at a plurality of positions of the carriage along the arcuate guide track, a focal plane of the ultrasound transducer is positioned within one or more of a cornea, anterior chamber, and lens of the eye; wherein a radius of curvature of the arcuate guide track is less than about 95 mm; wherein a radius of curvature of the arcuate guide track is less than about 75 mm; wherein a radius of curvature of the arcuate guide track ranges from about 25 mm to about 95 mm and further comprising: an enclosure positioned on a support surface, the enclosure having an interior volume and having a side wall to engage the patient; a window portion positioned in the side wall of the enclosure, the window portion being substantially acoustically and optically transparent; a border of the window portion operable to accept the imaging goggles; a first fluid disposed in the interior volume of the enclosure, the first fluid having a fluid level within the interior volume wherein the fluid level is above the window portion; a second fluid disposed in the volume of the imaging goggles between the eye of the patient and an interior surface of the imaging goggles, wherein the ultrasound transducer and arcuate track being positioned in the interior volume of the enclosure; and a linear track operably engaged with the arcuate guide track, wherein the ultrasound transducer is configured to record a plurality of A-scan images of the eye of the patient while the patient is wearing the imaging goggles when the imaging goggles are attached to the border of the window portion; and wherein a center of curvature of the arcuate guide track is positioned between the transducer and the cornea of the eye of the patient.

A method is disclosed comprising emitting ultrasound pulses while an ultrasonic transducer moves along an arcuate guide track; receiving ultrasound pulses reflected from an optical structure of an eye of a patient; and generating an image of the ocular structure, wherein a radius of curvature of the arcuate guide track is no more than about 95 mm.

The ultrasound imaging system can include an aspect wherein the radius of curvature of the arcuate guide track is less than about 75 mm; wherein the radius of curvature of the arcuate guide track is less than about 50 mm: wherein a radius of curvature of the arcuate guide track ranges from about 25 mm to about 95 mm and further comprising: providing an enclosure on a support surface, the enclosure having a window portion positioned in the side wall of the enclosure, wherein the window portion is substantially acoustically and optically transparent, and the enclosure is filled with a first fluid to a level above the window portion; providing imaging goggles wherein the goggle lenses are substantially acoustically and optically transparent and a second fluid is disposed in the volume of the imaging goggles between an interior surface of the imaging goggles and the eye of the patient; providing an ultrasound transducer imaging system in the first fluid, the ultrasound transducer imaging system comprising the ultrasound transducer operably interconnected to the arcuate track which is, in turn, interconnected to a linear track;

positioning the patient wearing the imaging goggles at the window portion of the enclosure with the imaging goggles engaged with a border of the window portion; and scanning the eye of a patent using the ultrasound transducer imaging system, wherein the ultrasound transducer records a plurality of A-scan images of the eye of the patient; and combining, by a computer, the plurality of A-scan images to form a B-scan image, the image of the ocular structure comprising the plurality of A-scan images; and wherein a radius of curvature of the arcuate guide track ranges from about 25 to about 75 mm, wherein the imaging goggles and ultrasound transducer are positioned relative to each other such that, at a plurality of positions of the carriage along the arcuate guide track, a focal plane of the ultrasound transducer is positioned within one or more of a cornea, anterior chamber, and lens of the eye.

The ultrasound imaging system can include an aspect wherein the focal plane of the ultrasound transducer is positioned in a lens of the eye as the carriage moves along at least most of the arcuate guide track; wherein the focal plane of the ultrasound transducer is positioned in a cornea of the eye as the carriage moves along at least most of the arcuate guide track; wherein the focal plane of the ultrasound transducer is positioned in an anterior or posterior chamber of the eye as the carriage moves along at least most of the arcuate guide track; wherein a focal point of the ultrasound transducer is positioned in a lens of the eye as the carriage moves along at least about 75% of a length of the arcuate guide track; wherein a focal point of the ultrasound transducer is positioned in a cornea of the eye as the carriage moves along at least about 75% of a length of the arcuate guide track; wherein the focal plane of the ultrasound transducer is positioned in an anterior or posterior chamber of the eye as the carriage moves along at least about 75% of the arcuate guide track.

The ultrasound imaging system can include an aspect further comprising: providing an enclosure on a support surface, the enclosure having a window portion positioned in the side wall of the enclosure, wherein the window portion is substantially acoustically and optically transparent, and the enclosure is filled with a first fluid to a level above the window portion; providing imaging goggles wherein the goggle lenses are substantially acoustically and optically transparent and a second fluid is disposed in the volume of the imaging goggles between an interior surface of the imaging goggles and the eye of the patient; providing an ultrasound transducer imaging system in the first fluid, the ultrasound transducer imaging system having an ultrasound transducer operably interconnected to an arcuate track; positioning the patient wearing the imaging goggles at the window portion of the enclosure with the imaging goggles being engaged with a border of the window portion; scanning the first and second eyes of the patent using the ultrasound transducer imaging system, wherein the ultrasound transducer records first and second sets of A-scan images of the first and second eyes of the patient, respectively; and combining, by a computer, a plurality of A-scan images in the first set to form a B-scan image of the first eye and a plurality of A-scan images in the second set to form a B-scan image of the second eye, wherein a radius of curvature of the arcuate guide track is no more than about 95 mm.

Another ultrasound imaging method is disclosed comprising generating, by the ultrasound imaging system, a first image of a first eye of a patient, a fixation light being viewable by a second eye of the patient, but not the first eye during the generation of the first image; and thereafter, generating, by the ultrasound imaging system, a different second image of the second eye of the patient, the fixation light being viewable by the first eye, but not the second eye, of the patient during generation of the second image.

The preceding is a simplified summary to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

The following definitions are used herein:

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The phrases at least one, one or more, and and/or are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

An acoustically reflective surface or interface is a surface or interface that has sufficient acoustic impedance difference across the interface to cause a measurable reflected acoustic signal. A specular surface is typically a very strong acoustically reflective surface.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to an eye component.

Accuracy as used herein means substantially free from measurement error.

Aligning means positioning the acoustic transducer accurately and reproducibly in all three dimensions of space with respect to a feature of the eye component of interest (such as the center of the pupil, center of curvature or boundary of the cornea, lens, retina, etcetera).

The anterior segment comprises the region of the eye from the anterior surface of the cornea to the posterior surface of the lens.

Automatic refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Auto-centering means automatically, typically under computer control, causing centration of the arc scanning transducer with the eye component of interest.

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

Center of rotation of the eye, there is a point within the eyeball that is more or less fixed relative to the orbit when the eye rotates in its orbit. It is considered that the center of rotation of an emmetropic eye (that is, a normal eye with about 20/20 vision) lies on the line of sight of the eye about 13.5 mm behind the anterior pole of the cornea when the line of sight of the eye is perpendicular to both the base line and the frontal plane.

Centration means substantially aligning the center of curvature of the arc scanning transducer in all three dimensions of space with the center of curvature of the eye component of interest (such as the cornea, pupil, lens, retina, etcetera) such that rays from the transducer pass through both centers of curvature. A special case is when both centers of curvature are coincident.

A composite image is an image that is made from the combination of multiple images merged onto a common co-ordinate system.

Compositing is the combining of images or image elements from separate sources into a single image. As used herein, compositing is achieved through digital image manipulation.

The term computer-readable medium as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

The terms determine, calculate and compute, and variations thereof, as used herein, are used interchangeably and include any type of methodology, process, mathematical operation or technique.

An eye speculum is an instrument or device for keeping the eyelids apart during an inspection of or a procedure on or an operation on the eye. Examples are made from plated steel wire or plastic. Luer's, Von Graefe's, and Steven's are the most common types.

Fiducial means a reference, marker or datum in the field of view of an imaging device.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

The home position of the imaging ultrasound transducer is its position during a registration process.

In this disclosure, imaging goggles are a form of eye wear that encloses the area surrounding the eye in order to retain water or saline between the anterior surface of the cornea of an eye and the interior surface of the imaging goggles. This form of goggle is used in ultrasound or optical imaging of one or both eyes by providing an acoustic and optical path for the beam of the imaging device wherein the path approximates the acoustical or optical properties of the eye.

An imaging ultrasound transducer is the device that is responsible for creating the outgoing ultrasound pulse and detecting the reflected ultrasound signal that is used for creating the A-Scans and B-Scans.

LASIK is a procedure performed on the cornea for correcting refractive errors, such as myopia, hyperopia, and astigmatism. Commonly, an excimer laser selectively removes tissue from the inside of the cornea, after it is exposed, by cutting a thin flap, so as to reshape the external shape of the cornea.

The term module as used herein refers to any known or later developed hardware, software, firmware, artificial intelligence, fuzzy logic, or combination of hardware and software that is capable of performing the functionality associated with that element. Also, while the disclosure is described in terms of exemplary embodiments, it should be appreciated that individual aspects of the disclosure can be separately claimed.

Ocular means having to do with the eye or eyeball.

Ophthalmology means the branch of medicine that deals with the eye.

Optical as used herein refers to processes that use light rays.

Pachymetery or corneal pachymetery is technically referred to as Time Domain Reflectometry ultrasound. A pulse of ultrasonic energy is sent toward the cornea and the time spacing of the returning echoes are used to arrive at corneal thickness.

Positioner or positioning mechanism means the mechanism that positions a scan head relative to a selected part of an eye. In the present disclosure, the positioner can move back and forth along the x, y or z axes and rotate in the β direction about the z-axis. Normally the positioner does not move during a scan, only the scan head moves. In certain operations, such as measuring the thickness of a region, the positioner may move during a scan.

Posterior means situated at the back part of a structure; posterior is the opposite of anterior.

Precise as used herein means sharply defined and repeatable.

Precision means how close in value successive measurements fall when attempting to repeat the same measurement between two detectable features in the image field. In a normal distribution precision is characterized by the standard deviation of the set of repeated measurements. Precision is very similar to the definition of repeatability.

The pulse transit time across a region of the eye is the time it takes a sound pulse to traverse the region.

Refractive means anything pertaining to the focusing of light rays by the various components of the eye, principally the cornea and lens.

Registration as used herein means aligning.

Scan head means the mechanism that comprises the ultrasound transducer, the transducer holder and carriage as well as any guide tracks that allow the transducer to be moved relative to the positioner. Guide tracks may be linear, arcuate or any other appropriate geometry. The guide tracks may be rigid or flexible. Normally, only the scan head is moved during a scan.

Sector scanner is an ultrasonic scanner that sweeps a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will be reflected directly back to that transducer when the beam is aligned perpendicular to a specular surface.

A track or guide track is an apparatus along which another apparatus moves. In an ultrasound scanner or combined ultrasound and optical scanner, a guide track is an apparatus along which one or more ultrasound transducers and/or optical probes moves during a scan.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

An ultrasonic scanner is an ultrasound scanning device utilizing a transducer that both sends and receives pulses as it moves along 1) an arcuate guide track, which guide track has a center of curvature whose position can be moved to scan different curved surfaces; 2) a linear guide track; and 3) a combination of linear and arcuate guide tracks which can create a range of centers of curvature whose position can be moved to scan different curved surfaces.

A vector refers to a single acoustic pulse and its multiple reflections from various eye components. An A-scan is a representation of this data whose amplitude is typically rectified.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein. By way of example, the phrase from about 2 to about 4 includes the whole number and/or integer ranges from about 2 to about 3, from about 3 to about 4 and each possible range based on real (e.g., irrational and/or rational) numbers, such as from about 2.1 to about 4.9, from about 2.1 to about 3.4, and so on.

The preceding is a simplified summary of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the disclosure. In the drawings, like reference numerals may refer to like or analogous components throughout the several views.

DETAILED DESCRIPTION OF THE DRAWINGS

Ultrasound Eye Scanning Apparatus

Figure 1:
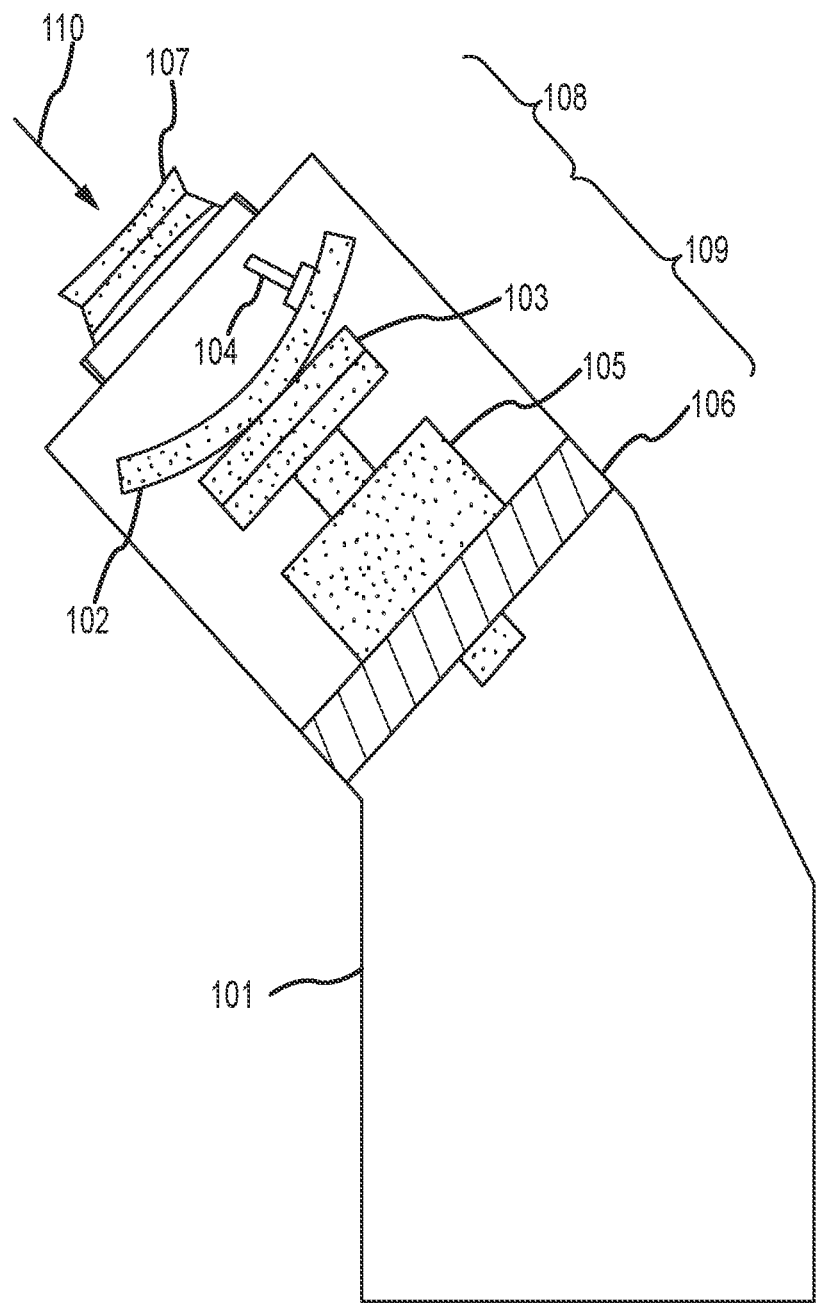
FIG. 1 is a schematic of the principal elements of a prior art ultrasound eye scanning device such as described in U.S. Pat. No. 8,317,709.

FIG. 1 is a schematic of the principal elements of a prior art ultrasound eye scanning device such as described in U.S. Pat. No. 8,317,709, entitled "Alignment and Imaging of an Eye with an Ultrasonic Scanner" which is incorporated herein by reference. The scanning device 101 of this example is comprised of a disposable eyepiece 107, a scan head assembly 108 and a positioning mechanism 109. The scan head assembly 108 is comprised of an arcuate guide 102 with a scanning transducer 104 on a transducer carriage which moves back and forth along the arcuate guide track 102, and a linear guide track 103 which moves the arcuate guide track 102 back and forth (as described further in FIG. 3). The positioning mechanism 109 is comprised of an x-y-z and beta mechanisms 105 (described in FIG. 4) mounted on a base 106. The base 106 is rigidly attached to the scanning device 101. A longitudinal axis 110 passes generally through a center of the head assembly 108 and is substantially perpendicular to a face of the eyepiece 107. A video camera (not shown) may be positioned within the scanning device 101 and aligned with the longitudinal axis 110 to provide an image of a patient's eye through the eyepiece 107. The scanning device 101 is typically connected to a computer (not shown) which includes a processor module, a memory module, a keyboard, a mouse or other pointing device, a printer, and a video monitor. One or more fixation lights (not shown) may be positioned within the scanning device at one or more locations. The eyepiece 107 may be disposable as described in FIG. 5.

The positioner assembly 109 and scan head assembly 108 are both fully immersed in water (typically distilled water) which fills the chamber from base plate 106 to the top of the chamber on which the eyepiece 107 is attached.

A patient is seated at the scanning device 101 with one eye engaged with the disposable eyepiece 107. The patient is typically directed to look downward at one of the fixation lights during a scan sequence. The patient is fixed with respect to the scanning device 101 by a headrest system such as shown, for example, in FIG. 4, and by the eyepiece 107.

An operator using a mouse and/or a keyboard and the video monitor, for example, inputs information into the computer selecting the type of scan and scan sequences as well as the desired type of output analyses. The operator using the mouse and/or the keyboard, the video camera located in the scanning machine, and the video screen, centers a reference marker such as, for example, a set of cross hairs displayed on the video screen on the desired component of the patient's eye which is also displayed on video screen. This is done by setting one of the cross hairs as the prime meridian for scanning. These steps are carried out using the positioning mechanism which can move the scan head in the x, x, z and beta space (three translational motions plus rotation about the z-axis). The z-axis is parallel to the longitudinal axis 110. Once this is accomplished, the operator instructs the computer to proceed with the scanning sequence. Now the computer processor takes over the procedure and issues instructions to the scan head 108 and the scanning transducer 104 and receives positional and imaging data. The computer processor proceeds with a sequence of operations such as, for example: (1) with the transducer carriage substantially centered on the arcuate guide track, rough focusing of the scanning transducer 104 on a selected eye component; (2) accurately centering of the arcuate guide track with respect to the selected eye component; (3) accurately focusing the scanning transducer 104 on the selected feature of the selected eye component; (4) rotating the scan head assembly 108 through a substantial angle (including orthogonal) and repeating steps (1) through (3) on a second meridian; (5) rotating the scan head back to the prime meridian; (6) initiating a set of A-scans along each of the of selected scan meridians, storing this information in the memory module; (7) utilizing the processor, converting the A-scans for each meridian into a set of B-scans and then processing the B-scans to form an image associated with each meridian; (8) performing the selected analyses on the A-scans, B-scans and images associated with each or all of the meridians scanned; and (9) outputting the data in a preselected format to an output device such as a printer. As can be appreciated, the patient's head must remain fixed with respect to the scanning device 101 during the above operations when scanning is being carried out, which in a modern ultrasound scanning machine, can take several tens of seconds.

An eyepiece serves to complete a continuous acoustic path for ultrasonic scanning, that path extending in water from the transducer to the surface of the patient's eye. The eyepiece 107 also separates the water in which the patient's eye is immersed (typically a saline solution) from the water in the chamber (typically distilled water) in which the transducer guide track assemblies are contained. The patient sits at the machine and looks down through the eyepiece 107 in the direction of the longitudinal axis 110. Finally, the eyepiece provides an additional steady rest for the patient and helps the patient's head to remain steady during a scan procedure.

Mechanisms for General Ultrasound Scanning

Figure 2:
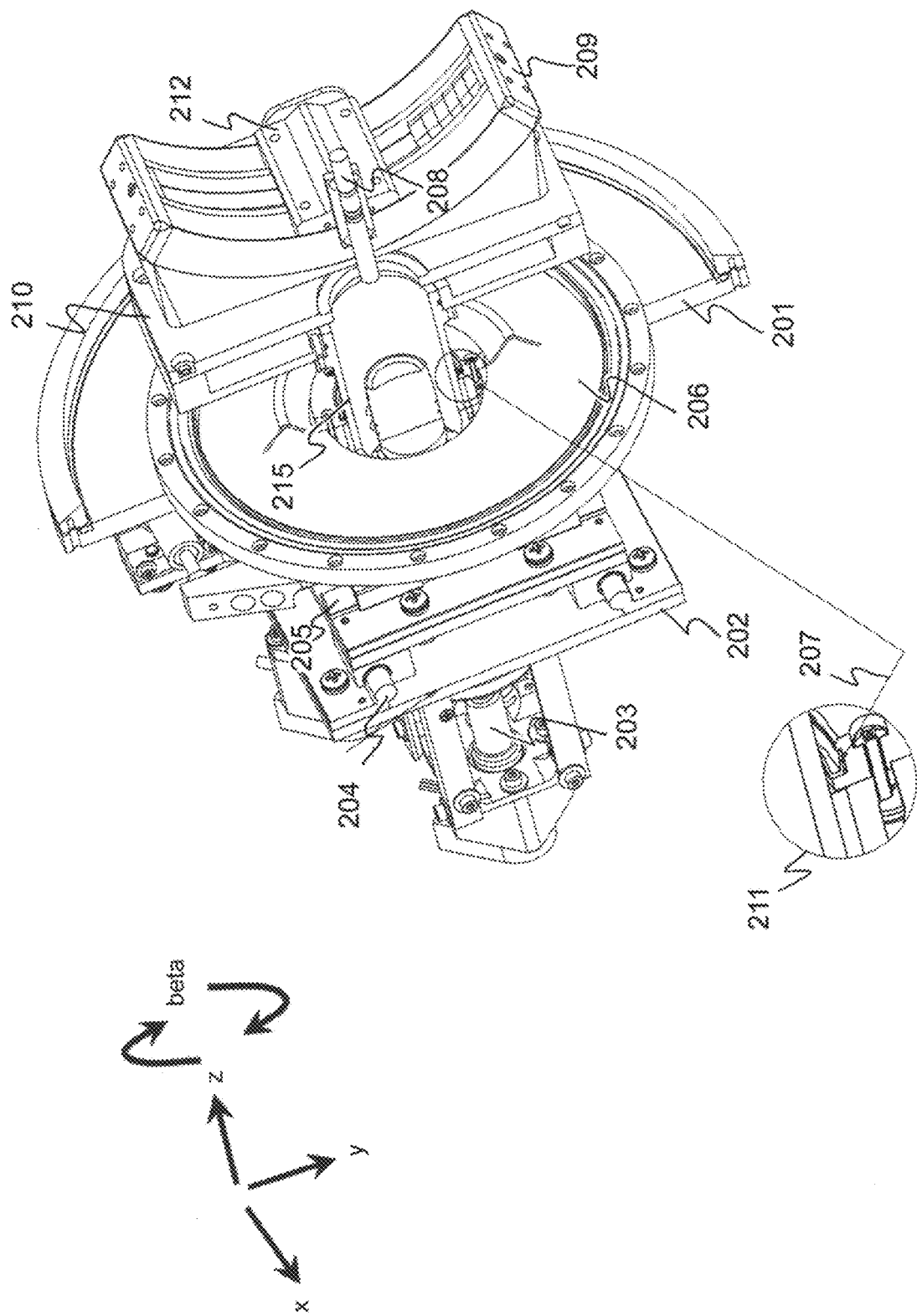
FIG. 2 illustrates a compact scan head positioning mechanism which has been disclosed previously in U.S. Pat. No. 8,758,252.

FIG. 2 illustrates a compact scan head positioning mechanism which has been disclosed previously in U.S. Pat. No. 8,758,252 entitled "Innovative Components for an Ultrasonic Arc Scanning Apparatus" which is incorporated herein by reference. FIG. 2 shows a prior art scan head assembly comprised of scan head mount structure 210 and an arcuate guide track 209. The arcuate guide track 209 is comprised of an ultrasonic transducer 208 mounted on a transducer carriage 212. The transducer carriage 212 can be moved back and forth along arcuate guide track 209 to perform an arc scan. The scan head assembly is attached to a main positioner arm 215 (shown in a sectional view).

The scan head mount structure 210, arcuate guide track 209, transducer carriage 212, and ultrasonic transducer 208, while immersed in water, are sealed from the rear portion of the positioning mechanism by a translational seal 206 and a combined z-axis and rotational seal 207. The translational seal 206 is typically formed by a large rubber membrane that can flex with the small x and y motions required by the scanning head positioner, although alternate sealing mechanisms may be employed. The combined z-axis seal and rotational seal 207 seal against the main positioner arm 215 which can both rotate and move in and out in the z-direction which lies substantially parallel to a longitudinal axis of an axial piston 203. Translational seal 206 is attached to a stationary plate 201 which, in turn, is affixed to the main arc scanner chamber (not shown) which, in turn, is fixed with respect to the patient being scanned. The combined z-axis and rotational seal 207, which is shown in close-up view 211, is typically formed by a circumferential groove type sealing mechanism with the groove facing into the water, although alternate sealing mechanisms may be employed. Available seals allow both rotation and axial translation of the main positioner arm 215 while maintaining a watertight seal. Plate 202 forms a platform for the x- and y-positioning mechanisms. Plate 202 is fixed relative to stationary plate 201. The scanning head assembly can be moved back and forth axially (the z-direction) by axial piston 203 or another suitable mechanism. The scanning head assembly can be rotated (the beta-direction) about the z-axis by a rotary stepping motor (not shown) or another suitable device. The scanning head assembly can be moved up and down (the y-direction) by piston 205 or another suitable mechanism. The scanning head assembly can be moved from side to side (the x-direction) by piston 204 or another suitable mechanism. The components to the left or rear of stationary plate 201 remain in ambient air while the components to the right or front of stationary plate 201 are in immersed in water when the arc scanner is operational.

Typically, the scan head assembly is moved in the x-, y-, z- and beta directions to position the scan head assembly with respect to an eye component of interest. Although these motions are typically made rapidly under computer control, scans of the eye are typically not made during positioning. Once the scan head assembly is positioned with respect to the eye component of interest, scans are made by the transducer carriage 212 moving back and forth along the arcuate guide track 209. As described in U.S. Pat. No. 8,758,252 which is incorporated herein by reference, the transducer carriage 212 moves along arcuate guide track 209 on a fluid bearing for smooth operation.

As described above, the scanning head assembly can be moved back and forth axially (the z-direction); rotated (the beta-direction) about the z-axis; moved up and down (the y-direction); and moved from side to side (the x-direction). It is therefore possible to move the entire scan head assembly in more complex motions by coordinating these movements to obtain scans that cannot be obtained by a simple arc scan. However, the mechanisms of the apparatus of FIG. 2, while suitable for rapid positioning movements, are not well-suited for rapid scanning motions necessary, for example, to obtain multiple images of an eye accommodating in real time. A more advanced device is illustrated in FIG. 3.

Figure 3:
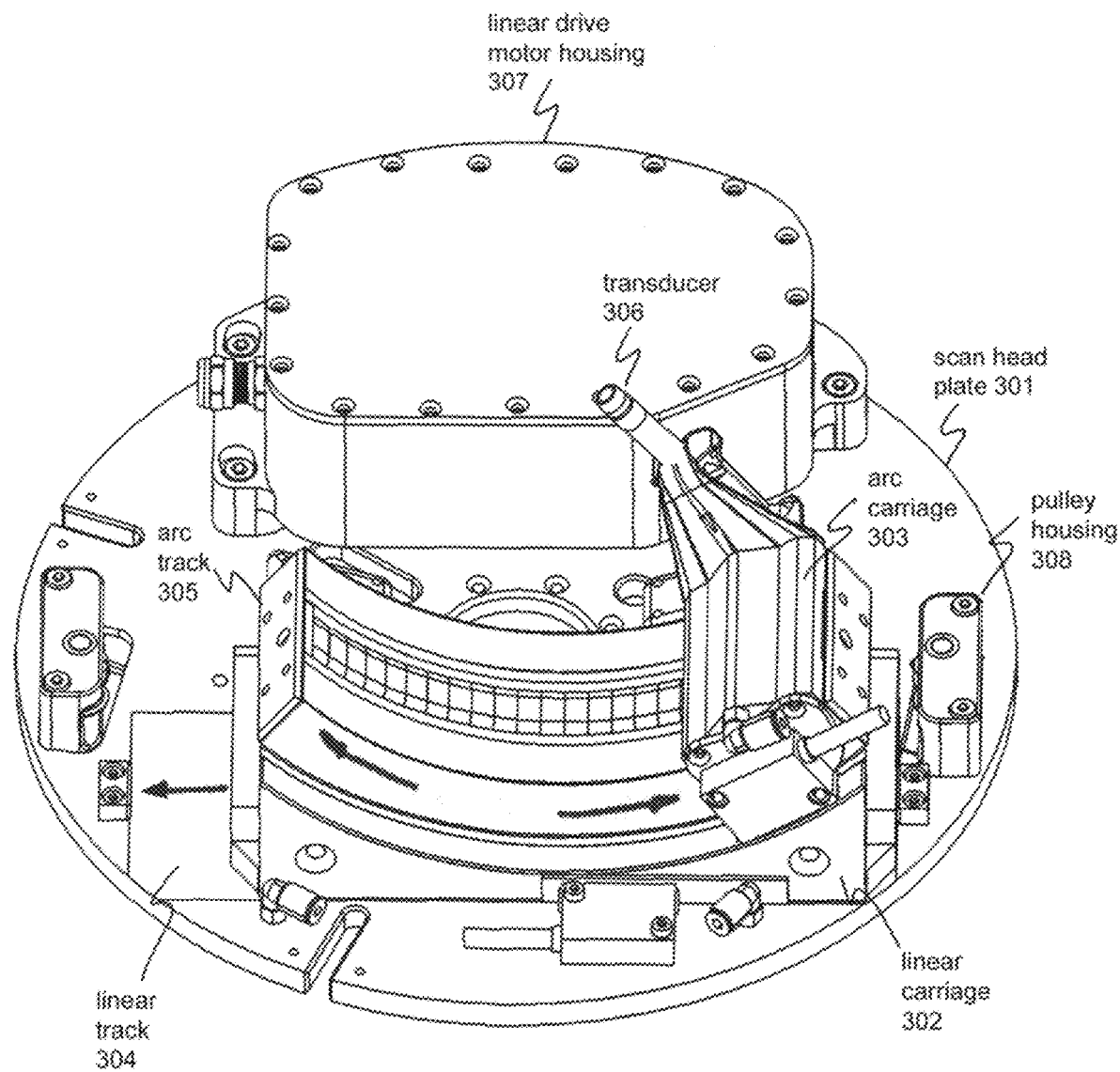
FIG. 3 illustrates a compact scan head mechanism which has been disclosed previously in U.S. Pat. No. 8,758,252.

FIG. 3 illustrates a prior art scan head capable of linear motion, arcuate motion, and combined linear and arcuate motion. This scan head was disclosed previously U.S. Pat. No. 8,317,709 which is incorporated herein by reference. A scan head plate 301 replaces scan head mount structure 210 of FIG. 2. Scan head plate 301 serves as the platform for a computer controlled linear carriage 302 and an arcuate carriage 303. Linear carriage 302 moves back and forth along a linear guide track 304. Arcuate carriage 303 moves back and forth along arcuate guide track 305. Typically, one of more transducers 306 or probes are mounted on the arcuate carriage 303. In this view, arc carriage 303 is at the rightmost limit of its travel along arcuate guide track 305 and linear carriage 302 is also at the rightmost limit of its travel on linear guide track 304. As can be appreciated, the motions of arcuate carriage 303 and linear carriage 302 can be controlled independently. For example, arcuate carriage 303 can move along arcuate guide track 305 or be parked anywhere along arcuate guide track 305 while linear carriage 302 moves along linear guide track 304. As another example, linear carriage 302 can be stationary while arcuate carriage 303 moves back and forth along arcuate guide track 305 to execute a pure arc scan. When arcuate carriage 303 is stationary and linear carriage 302 is moved, this is referred to as a linear scan. When both arcuate carriage 303 and linear carriage 302 are moved, this is referred to as combined scan. In this configuration, arcuate carriage 303 is moved along arcuate guide track 305 by an induction motor as described in U.S. Pat. No. 8,758,252, carriage 303 moves along arcuate guide track 305 on a fluid bearing which is also described in U.S. Pat. No. 8,758,252. In the example of FIG. 3, an ultrasound scanning transducer 306 is mounted on the arcuate carriage 303. A longitudinal axis which passes generally through a center of the ultrasound scanning transducer 306 is aligned substantially parallel to a radius of curvature of arcuate guide track 305. Linear carriage 302 is moved along linear guide track 304 by a drive motor (not shown) housed in linear drive motor housing 307. This drive motor moves linear carriage 302 by a belt and pulley system (not shown except for typical pulley housing 308). Linear carriage 302 moves along linear guide track 304 on a fluid bearing similar to that used between arcuate carriage 303 and arcuate guide track 305. In operation, the scan head assembly of FIG. 3 is under water and is sealed from the x, y, z, beta positioner by a sealing means behind the scan head plate 301. Thus the entire scanning mechanism is positioned with respect to an eye for scanning by the x, y, z, beta positioner shown in FIG. 2, while the actual acoustic imaging scan motion is implemented by one or both of the linear and arcuate carriages 302 and 303. The scan head assembly of FIG. 3 allows rapid independent linear and arcuate motion combinations of the ultrasound scanning transducer such that various scan geometries can be implemented to image not only the cornea, iris and anterior lens surface, but also the posterior lens surface, the sulcus, the ciliary body, the suprachoroidal space and the zonules that attach the lens to the ciliary body.

The scan head assembly of FIG. 3 may also perform a controlled combined motion where the linear and arcuate motions are coordinated to produce a resultant pure arcuate motion of the arcuate probe carriage wherein the effective radius of curvature of the arcuate track is larger or smaller than the radius of curvature of the arcuate guide track. This combined motion is more completely is described in U.S. Pat. No. 8,317,709.

Figure 4:
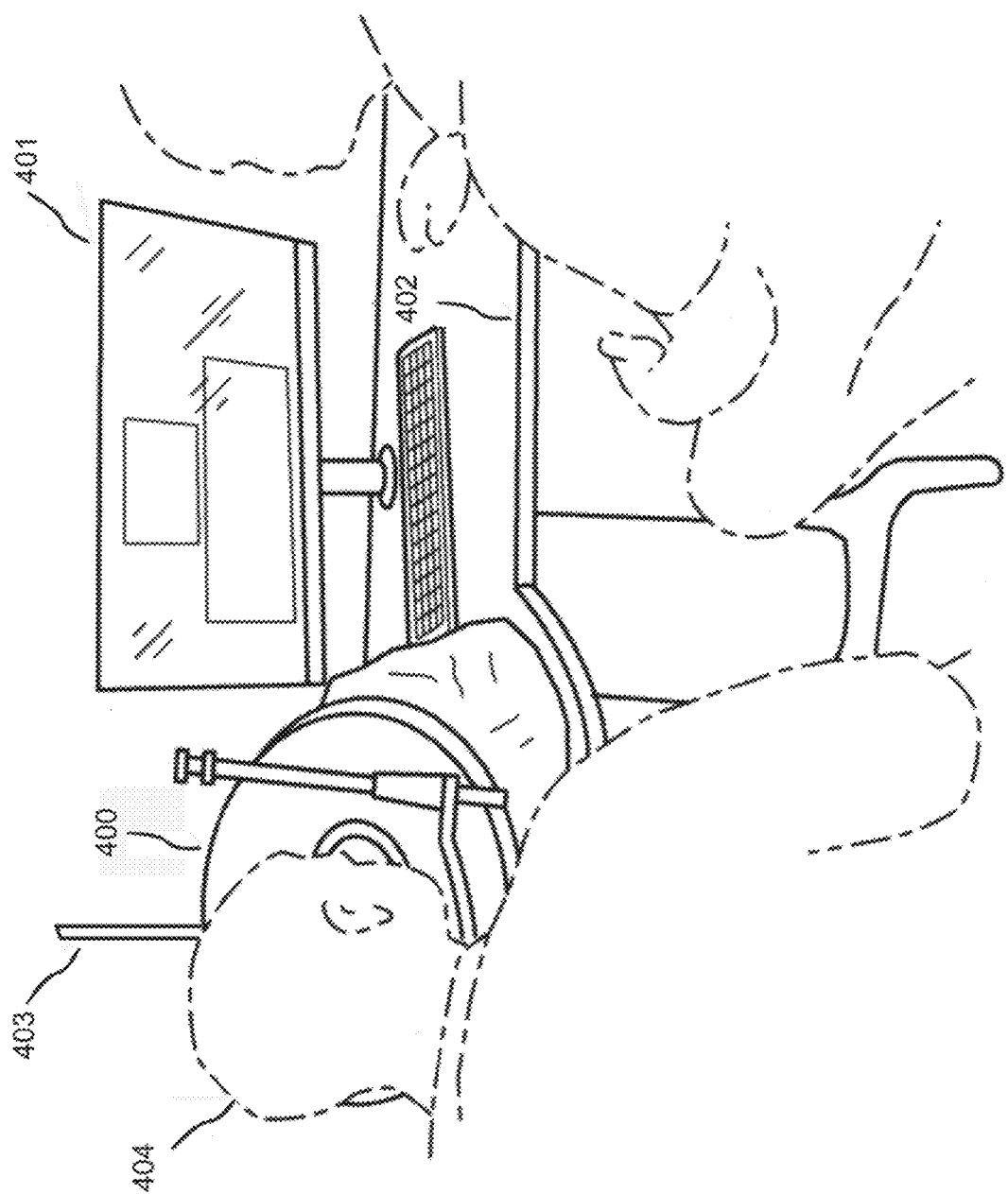
FIG. 4 shows another view of a prior art Insight 100™ Ultrasound Scanner in Use.

FIG. 4 shows a prior art Insight 100™ ultrasound scanner in use. The Insight 100™ shown in FIG. 4 includes the instrument itself 400, a large display monitor 401 and a custom table 402 on which the instrument 400 and monitor 401 are mounted. A computer and fluidics module are mounted under the table. A saline bag (not shown) is mounted on a pole 403 which extends above the patient's head 404. The saline bag provides saline for the eyepiece which separates the water in which the patient's eye is immersed from the water in the chamber in which the positioner and scan head assemblies are immersed. The eye piece is fully described in FIG. 7.

Figure 5:
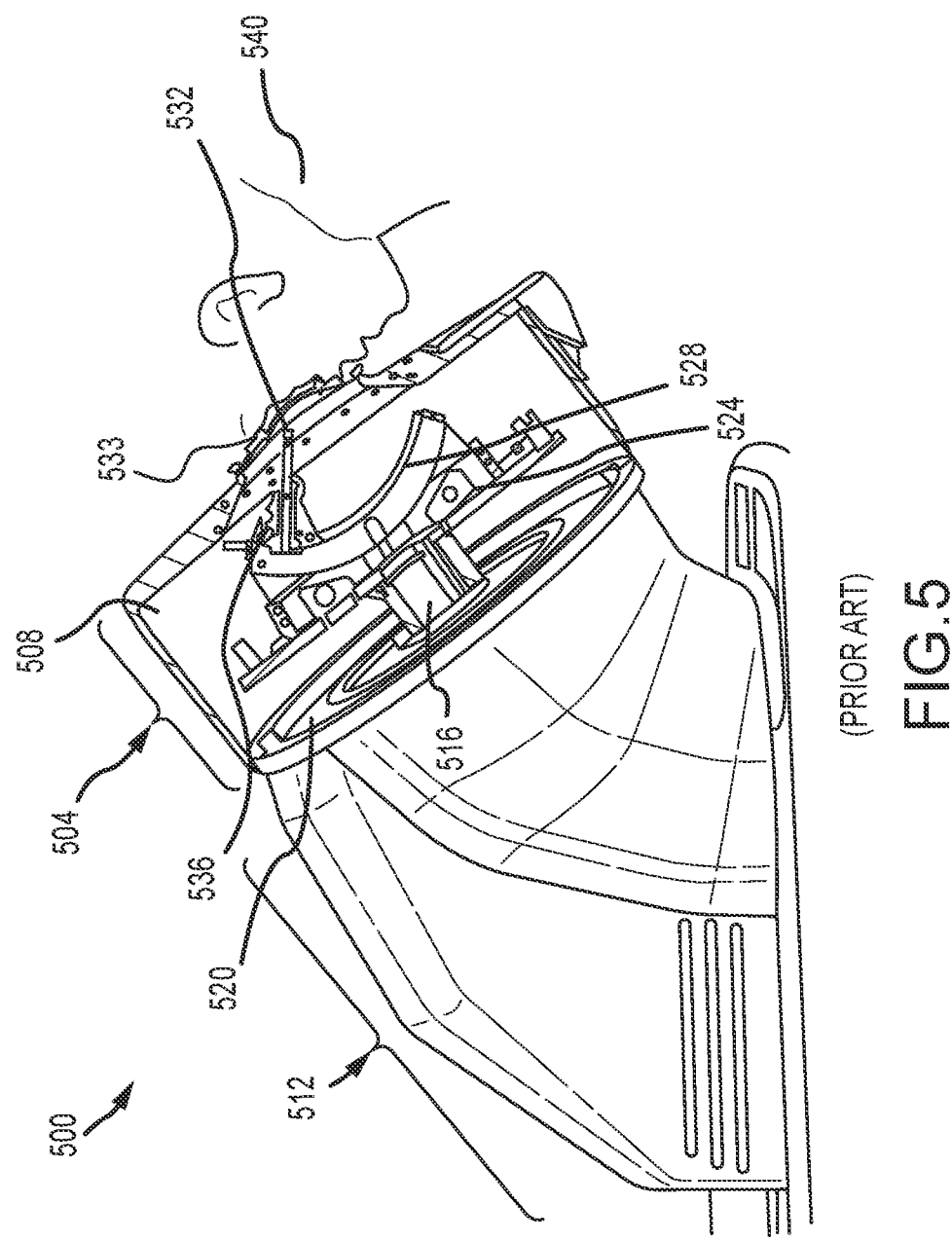
FIG. 5 is a cut-away of a prior art Insight 100™ with a patient in position for imaging.

FIG. 5 is a schematic cutaway drawing of a prior art Insight 100™ instrument 500. The scan head 504 is immersed in distilled water within a distilled water chamber 508 (shown in cut away view). The distilled water chamber 508 is attached to and separated from a housing which contains the instrument electronics and the positioner mechanism 512. The housing is open to ambient air. A telescoping shaft 516 of the positioner mechanism 512 passes through a large, flexible sealing membrane 520 into the distilled water chamber 508 and the scan head 504 is attached to the immersed end of this shaft 516. The scan head 504 comprises a linear track 524 on which is mounted an arcuate track 528. An ultrasound transducer 532 is mounted on a carriage 536 which can move along the arcuate track 528. In FIG. 5, a patient 540 is shown with one eye pushed against an eye piece such as described in more detail below in FIG. 6.

Figure 6:
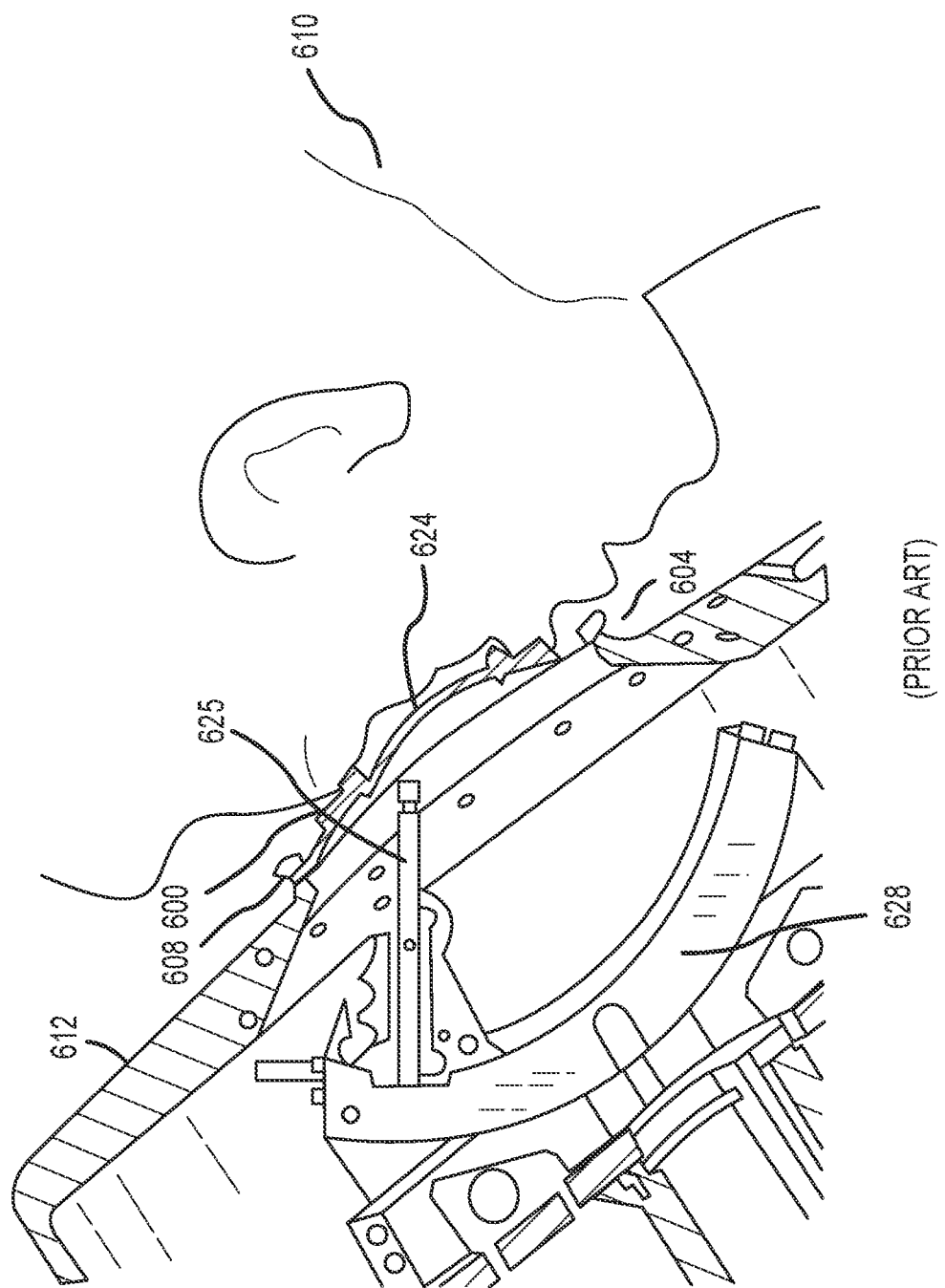
FIG. 6 is a schematic showing the relationship between the ultrasound transducer, the eye seal and the patients eye during imaging.

FIG. 6 is a cutaway view of the arc scanner 612 with patient 610 in position for scanning. The patient's eye socket is pressed against the soft flexible sealing ring 600 of the eye piece 604 which is now attached to the mounting ring 608 which, in turn, is attached to the main scanner housing 612 as described in FIG. 5. An ultrasound probe 625 is shown at the top end of the arcuate guide track 628 and is aimed at the patient's eye. As the probe 625 moves back and forth along the arcuate guide track 628, it's long axis remains approximately perpendicular to the surfaces of the cornea and anterior lens of the patient's eye. The tip of the ultrasound transducer comes very close to the membrane that separates the distilled water in the instrument bucket from the saline solution in the eye piece. The transducer is attached to the transducer carriage 613 by small magnets which will release the probe 625 if it contacts the membrane 624 of the eye piece 604 with enough force to endanger the patient's eye.

Figure 7:
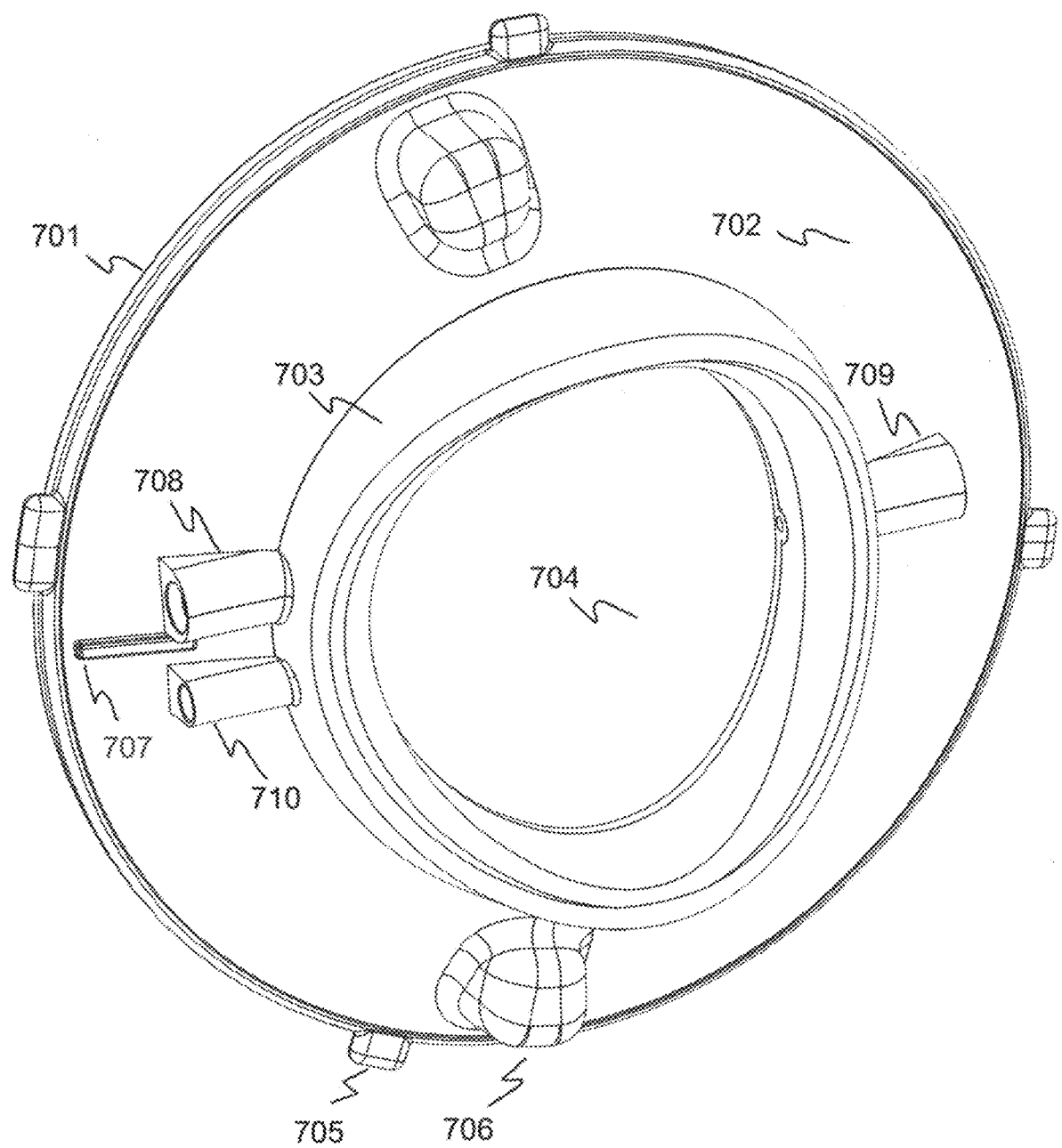
FIG. 7 is a schematic of a prior art eye piece used on the Insight 100™.

FIG. 7 is a schematic of a prior art eye seal first disclosed in U.S. Pat. No. 8,758,252 entitled "Innovative Components for an Ultrasonic Arc Scanning Apparatus". An eyepiece serves to complete a continuous (substantially constant acoustic impedance) acoustic path for ultrasonic scanning, that path extending from the transducer to the surface of the patient's eye. The eyepiece also separates the water in which the patient's eye is immersed from the water in the chamber in which the positioner and scan head assemblies are immersed. Finally, when the patient is in position for a scan with his or her head firmly against the eye piece, the eyepiece provides a reference frame for the patient and helps the patient's head to remain steady during a scan. The eyepiece also must be able to pass optical wavelengths of light so that fixation targets can be used to focus the patient's eye in a desired focal state and alignment with respect to the eye's visual or optical axis.

Eye piece 701 is comprised of a plastic base 702 molded from a plastic such as ABS and a soft rubber conformable face seal 703 formed from a silicone thermo-plastic elastomer. The conformable face seal 703 is over-molded onto the plastic base 702 by a heat process typically applied to the conformable face seal 703. Plastic base 702 also includes attaching mechanisms 705 which attach the eye piece to the mounting ring (not shown) which is typically attached to the main scanner housing; thumb and finger protrusions 706 used to rotate the eye piece into the mounting ring; indexing ridge 707 which prevents over-rotation of the eye piece as it is rotated into the mounting ring attached to the main scanner housing; and fill port 708, vent port 710 and drain port 709. Ports 708, 709 and 710 allow fluid flow through the eye piece base 701.

The eye piece is attached and sealed to a mounting ring which is, in turn, attached to the main scanner housing by a groove molded as part of the eye piece base 702 and a matching tongue formed as part of the mounting ring. The eye piece is rotated into position with the mounting ring where the tongue and groove form a contact connection which compresses and seals as the parts are rotated into position.

A sealed hygienic barrier membrane (not shown) is formed as part of the eye piece and is typically located, where the soft rubber face seal 703 is connected to the eye piece base 701. This membrane is typically attached onto the plastic eye piece base 702 by an adhesive backing commonly used in medical disposable components. The thickness of the membrane is designed for transmission of light (such as the fixation targets shown in FIG. 3) and transmission of acoustic energy (emitted by the transducer and reflected by a component of the eye). The membrane is hermetically sealed to prevent saline solution from contaminating the distilled water in the machine body (saline solution or tap water inside the machine body can corrode plastic, ceramic and metal components) and to prevent the distilled water in the machine body from contaminating the saline solution in the eye piece. As disclosed in U.S. Pat. No. 8,758,252, eye piece membranes have been made from materials such as, for example, polyethylene, mylar, polypropylene; vinylidene chloride; polyvinylidene chloride; or DuraSeal (made by Diversified Biotech) which is polyethylene based material free of adhesives. A preferred material is medical grade polyethylene which has an acoustic impedance slightly higher than that of water (about 2.33 million $kg/m^2$-s compared to 1.54 million $kg/m^2$-s for water). The thickness of the membrane is preferably in the range of about 10 to about 30 microns. This thickness is a small part of an acoustic wavelength in water which is about 150 microns at 10 MHz and about 20 microns at 80 MHz.

The fill, drain and vent ports shown in FIG. 7 are designed and sized for fast fill (to minimize the patient's time with their eye immersed in the saline solution), for venting of any bubbles that may form, for example, if the seal on the patient's head leaks or the patient pulls away from the machine, and for rapid draining of the saline solution back into the plastic saline bag after scanning is completed. As can be appreciated, the fill and vent ports are on the top of the eye piece and the drain port is on the bottom of the eye piece.

Figure 8:
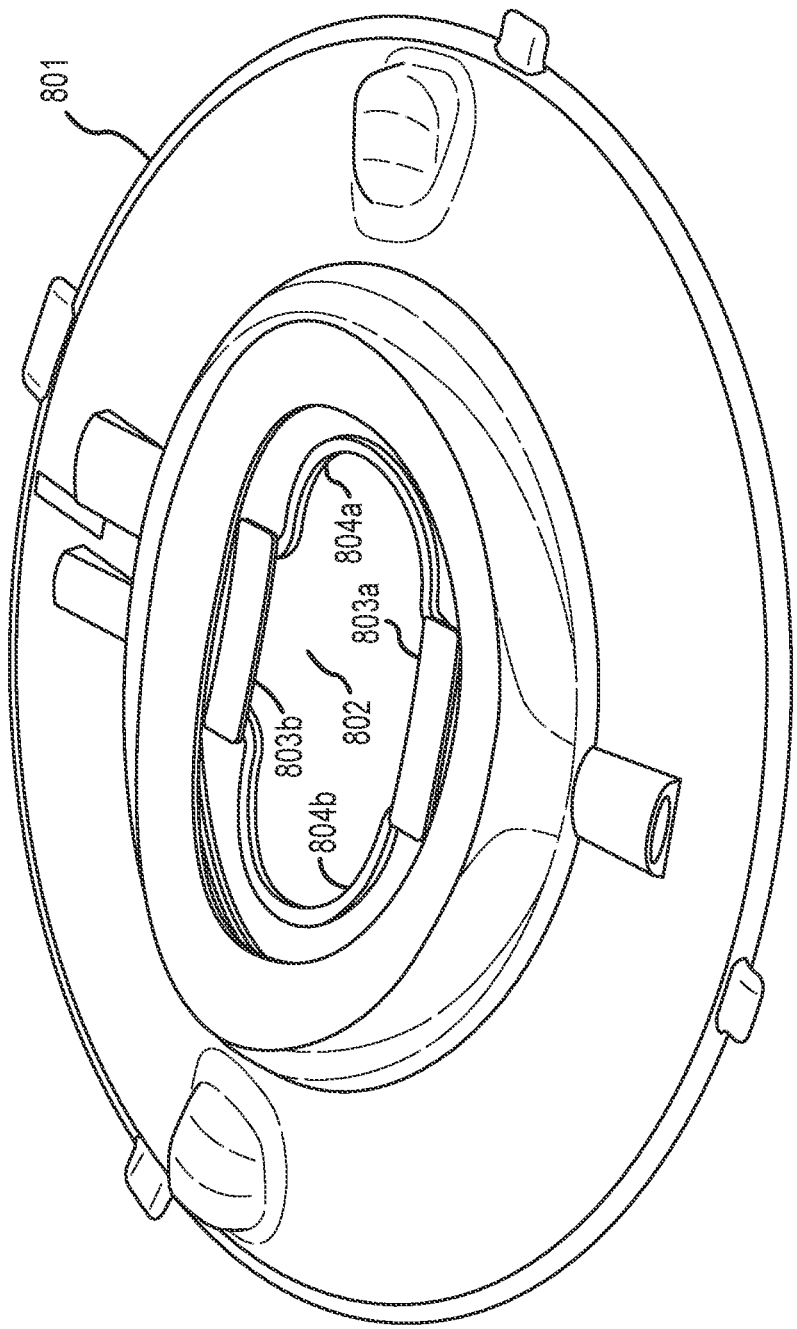
FIG. 8 is a schematic of a speculum that fits inside the eye piece of FIG. 7.

FIG. 8 is a schematic of the speculum of an embodiment as it would fit inside an eye piece 801. The speculum fits on the inner side of the sealed hygienic barrier membrane 802 that separates the saline solution into which the patient's eye is immersed from the distilled water in the imaging machine. The speculum comprises opposing pads 803a and 803b optionally comprising an adhesive to adhere to skin of a patient and a flexible eyelid retraction member 804a and 804b engaging the opposing pads 803a and 803b. FIG. 8 illustrates how the speculum would rest on the hygienic barrier membrane 802 of the eyepiece 801. The length of this speculum is about 1.70 inches, the width is about 1.05 inches and the height is about 0.7 inches. The speculum shown is typically fabricated from a thermoplastic plastic by a process such as, for example, injection molding.

Figure 9:
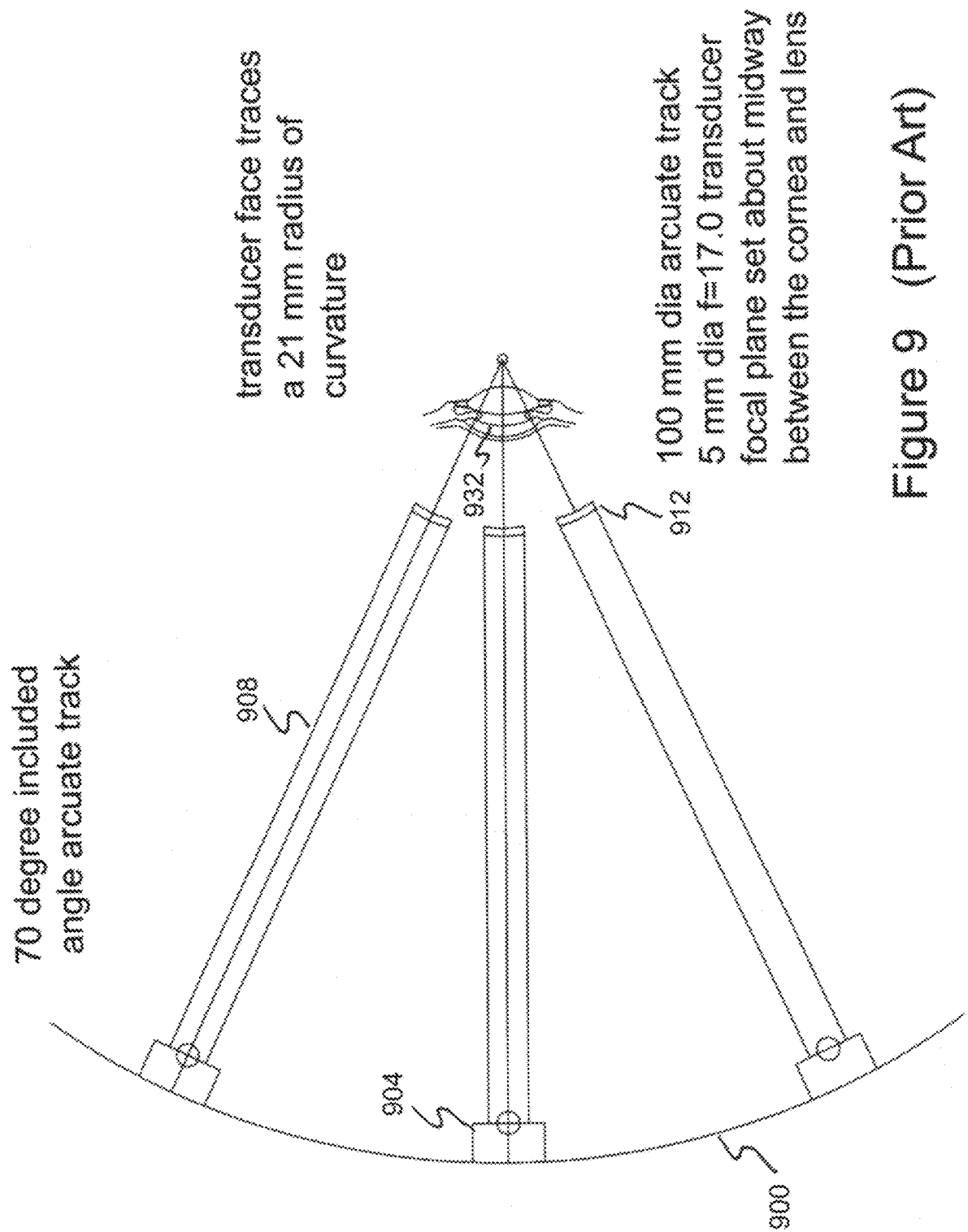
FIG. 9 is a schematic of an Insight 100™ arcuate track, a transducer holder and transducer in relation to an eye in position for scanning.
Figure 10:
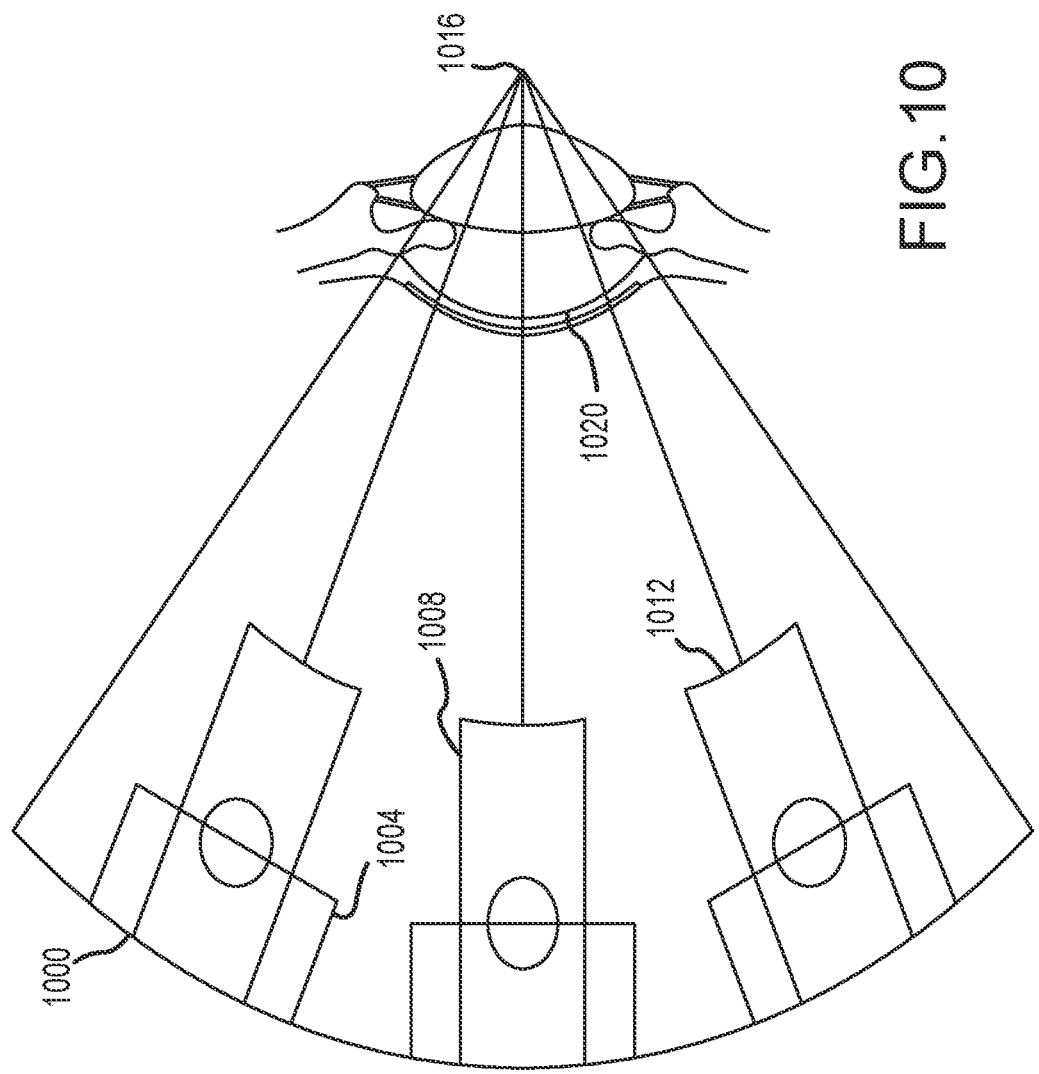
FIG. 10 is a schematic of an arcuate track, a transducer holder and transducer in relation to an eye in position for scanning as proposed for an ultrasound imaging system according to the present disclosure.

FIG. 9 is a schematic of an Insight 100™ arcuate track 900, a transducer holder 904 and transducer 908 in relation to an eye 920 in position for scanning. The arcuate track 900 allows the transducer 908 to be moved through an angle of 70 degrees. The arcuate track 900 has a radius of curvature of 100 mm. The transducer 908 is attached to a transducer holder 904. The face 912 of the transducer 908 is 21 mm from the center of curvature 916. The focal length of the transducer is typically 17 mm but can be changed, by changing the transducer, to any focal length between about 12 mm to about 21 mm. In FIG. 10, the focal point or plane 932 of the transducer 908 is shown as being located in the anterior chamber about halfway between the posterior surface of the cornea 924 and the anterior surface of the lens 928.

FIG. 10 is a schematic of an arcuate track 1000, a transducer holder 1004 and transducer 1008 in relation to an eye in position for scanning as proposed for an ultrasound imaging system according to the present disclosure. The arcuate track 1000 allows the transducer 1008 to be moved through an angle of 80 degrees. The arcuate track 1000 has a radius of curvature of 32 mm. The transducer 1008 is attached to a transducer holder 1004. The face 1012 of the transducer 1008 remains at 21 mm from the center of curvature 1016. The focal length of the transducer shown as 12.7 mm but can be changed, by changing the transducer, to any focal length between about 10 mm to about 21 mm. In FIG. 10, the focal point or plane 1020 of the transducer 1008 is shown as being located at about the midpoint of the cornea 924.

The geometry of the arcuate track 1000 of FIG. 10 is based on shrinking the arcuate track 1000, the transducer 1008, and/or transducer holder 1004 to about ⅓ of its former size. The range of motion of the transducer 1008 is preserved and even increased from a 70 degree included angle to an 80 degree included angle. The obvious benefit is a reduction in size of the entire scan head. A less obvious benefit is that an arcuate sweep can be made in about a third of the time as the original geometry of FIG. 9. This reduction of sweep time does not require a change in the velocity of the transducer carriage along the arcuate track.

Present Disclosure

Figure 11:
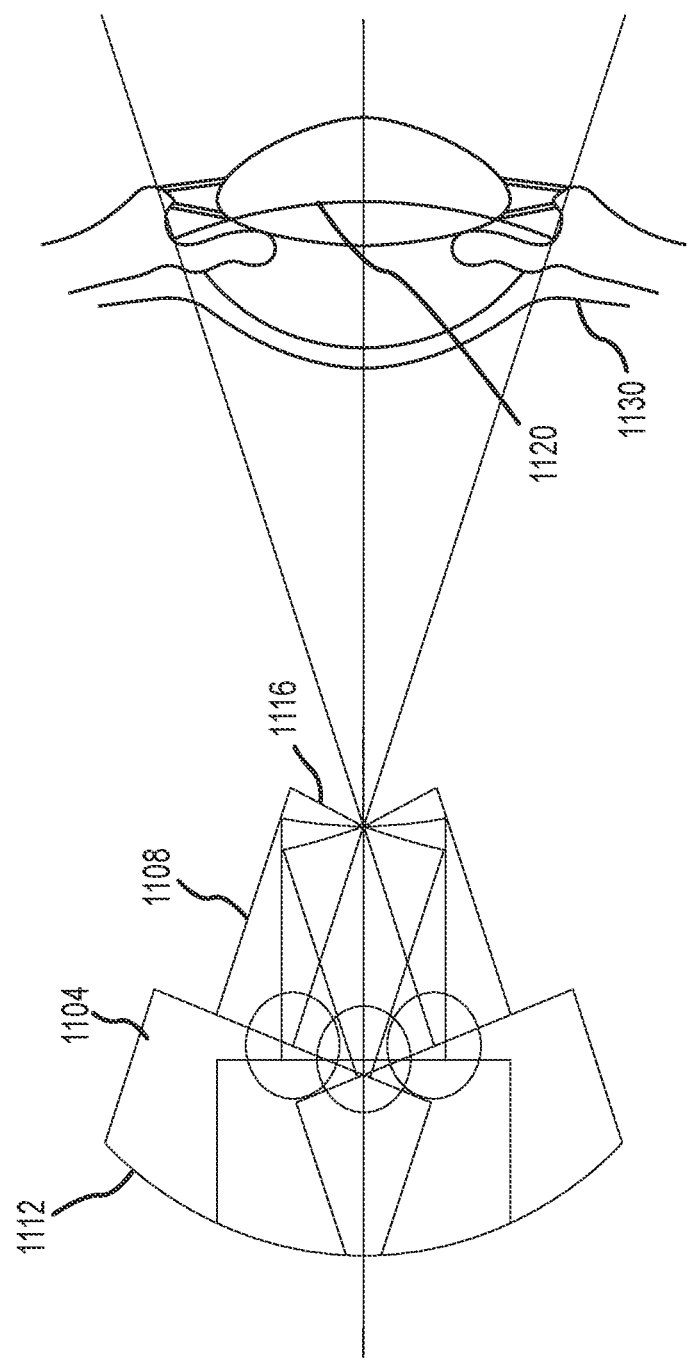
FIG. 11 is a schematic of a sector scanner mechanism showing a transducer holder and transducer in relation to an eye in position for scanning as an alternate proposed for an ultrasound imaging system according to the present disclosure.

FIG. 11 is a schematic of a scanner mechanism showing a transducer holder 1104 and transducer 1108 in relation to an eye 1130 in position for scanning as an alternate proposed for an ultrasound imaging system according to the present disclosure. The arcuate track 1112 allows the transducer 1108 to be moved through an angle of 40 degrees. The arcuate track 1112 has a radius of curvature such that the center of curvature is at the center point of the transducer face 1116. This emulates the action of a sector scanner. The transducer 1108 is attached to a short transducer holder 1104. The face 1116 of the transducer remains at 21 mm from the center of curvature 1100 of the arcuate track. The focal length of the transducer is shown as 12.7 mm but can be changed, by changing the transducer, to any focal length between about 10 mm to about 21 mm. In FIG. 11, the focal point or plane 1120 of the transducer 1108 is shown as being located inside the lens.

The geometry of the mechanism of FIG. 11 is based on shrinking the arcuate track and transducer holder to about ⅓ of its former size. The range of imaging of the transducer is such that coverage of the distal end of the lens is increased and does not require the patient to move or rotate their eye to obtain coverage of the ends of the lens, the ciliary sulcus and the zonules. The obvious benefit is a reduction in size of the entire scan head. Another benefit is that an arcuate sweep can be made in about a third of the time as the original geometry of FIG. 9. This reduction of sweep time does not require a change in the velocity of the transducer carriage along the arcuate track. The velocity of the transducer carriage is limited by cavitation in the distilled water in which the scan head is immersed.

The scan head configurations described in FIGS. 10 and 11 can lead to a substantial reduction in size and weight of the positioning and scan head mechanisms over those of the Insight 100™. The proposed positioning and scan head mechanisms are approximately one third the size of those of the Insight 100™ with no loss of functionality. Each can yield a slightly wider angle coverage of the eye compared with the Insight 100™ configuration described in FIG. 9.

The linear and arcuate track mechanisms that move the transducer carriage under computer control can move on either fluid bearings as used on the Insight 100™ or solid-surface bearing plates made from materials such as Teflon. The use of solid bearings eliminates the maintenance associated with the small orifices that are used in the fluid bearing system.

Figure 12:
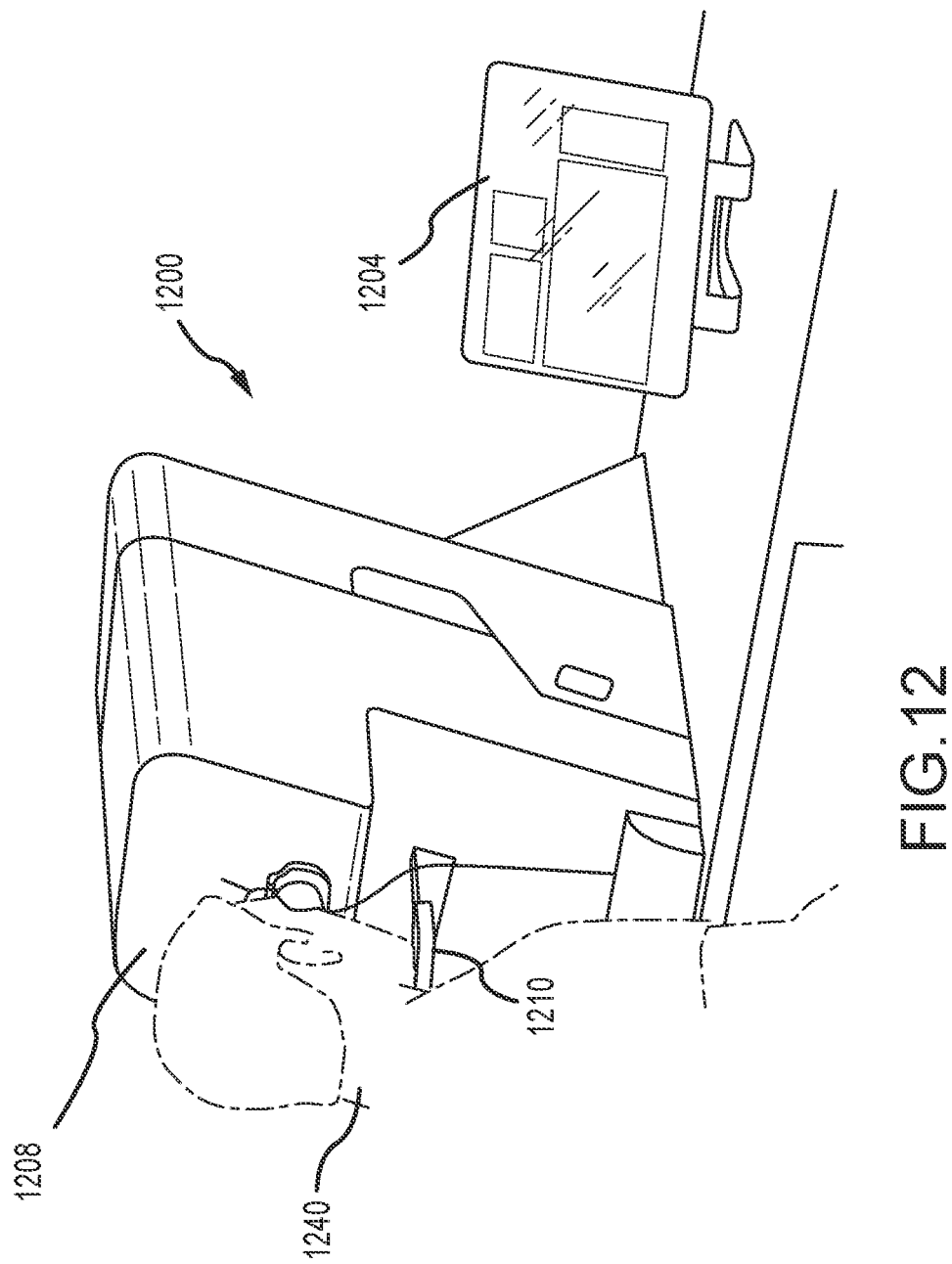
FIG. 12 is a rendering of an ultrasound imaging system according to the present disclosure with a patient in position to be scanned.

FIG. 12 is a rendering of an ultrasound imaging system 1200 according to the present disclosure with a patient 1240 in position to be scanned. The ultrasound imaging system 1200 is now a self-contained desktop device with only a moveable monitor 1204 being separate. It is similar in size and weight to other ophthalmic imaging instruments such as the IOL Master™, the Optivue™ and Topcon OCT™ systems.

As can be seen, the Insight 100™ such as shown in FIG. 4, is comprised of the instrument which is built into its own custom designed table. The imaging and control computer as well as the fluidics module are mounted under the table. The Insight 100™ therefore takes up considerable space in a clinic and must be disassembled to be moved.

With the ultrasound imaging system 1200 shown in FIGS. 12, the body of the instrument 1208 is filled with distilled water in which the scan head moves. The control and image processing computer and memory (not shown) are now on a circuit board situated within the electronics section of the desktop device which is internal to the instrument housing. The computer monitor 1204 is now decoupled from the instrument and can be a stand-alone monitor, a tablet or a cell phone which communicates with the on-board computer via short-range wireless connection. The user interface of the ultrasound imaging system 1200 is improved and can display more control and imaging information than the interface developed for the Insight 100™.

Figure 14:
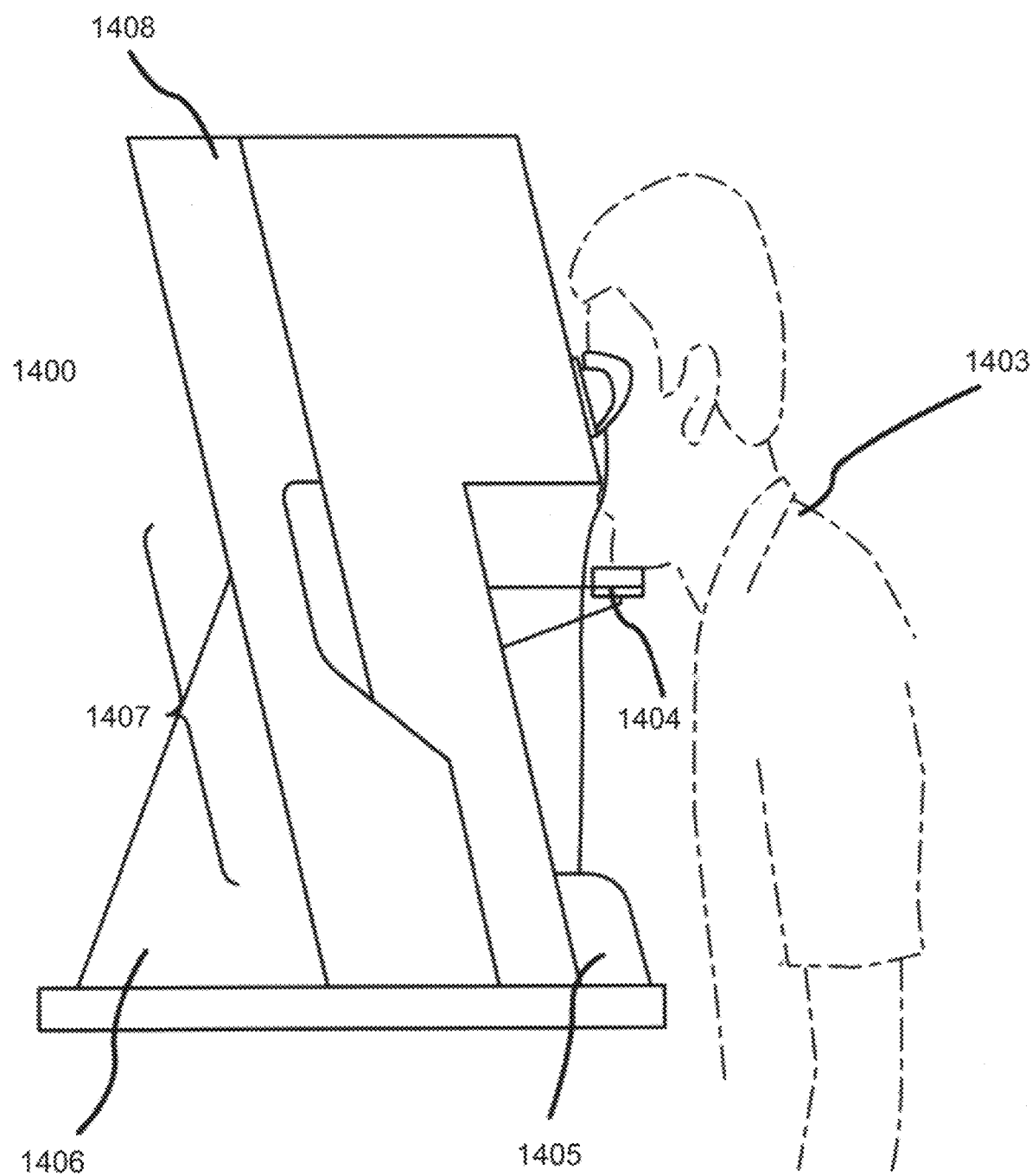
FIG. 14 is another rendering for an ultrasound imaging system with a patient in position to be scanned, according to the present disclosure.
Figure 15:
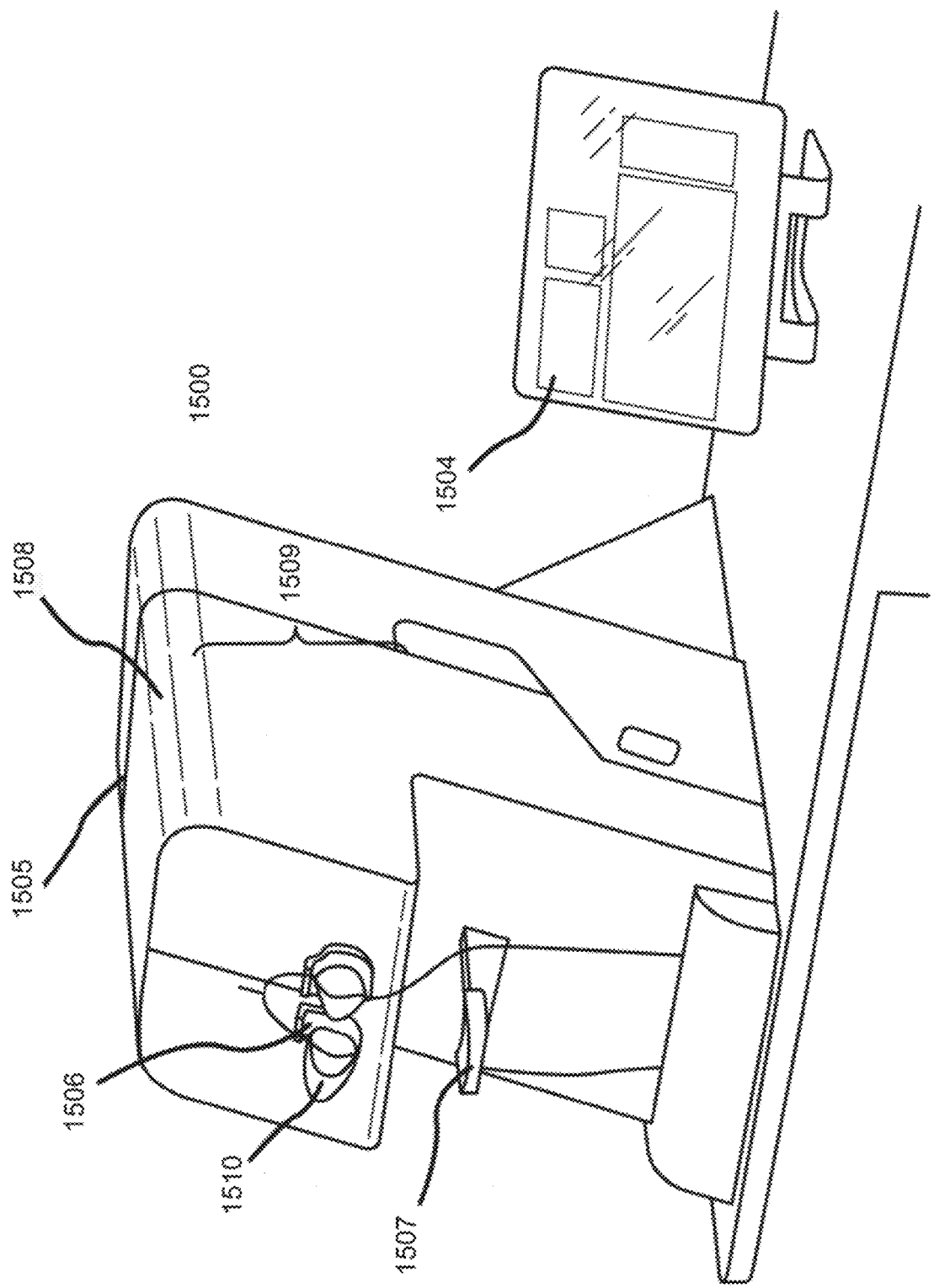
FIG. 15 is another rendering of an ultrasound imaging system according to the present disclosure.

The distilled water system and its reservoir are also contained inside the rear of the device 1208 housing as shown in FIG. 14. A saline bag (not shown) can be placed in a compartment inside the instrument housing as shown in FIG. 15. The saline solution can be warmed to body temperature for patient comfort. Any saline that leaks out of the imaging goggles 1300 is captured by a used saline catch bin within the lower portion of the housing as shown in FIG. 14.

The distilled water in the instrument can be treated for biological contaminants as it is circulated within the instrument by passing the distilled water through an ultraviolet light source.

In another embodiment, the ultrasound imaging system 1200 uses the contralateral (opposite or second) eye for fixation and possibly focusing while a first eye of the patient is being scanned. Basically, the eye being scanned is kept in the dark as there is no flashing when the scan head moves in front of the fixation light to reduce dilation/constriction of the eye being imaged) while the opposite eye that is not currently being imaged is used to look at a fixation light and possibly even a small screen to allow for focusing.

The chin rest 1210 on the ultrasound imaging system according to the present disclosure is adjustable. There are small buttons on the side of the device for the patient to adjust the chin rest.

Figure 13:
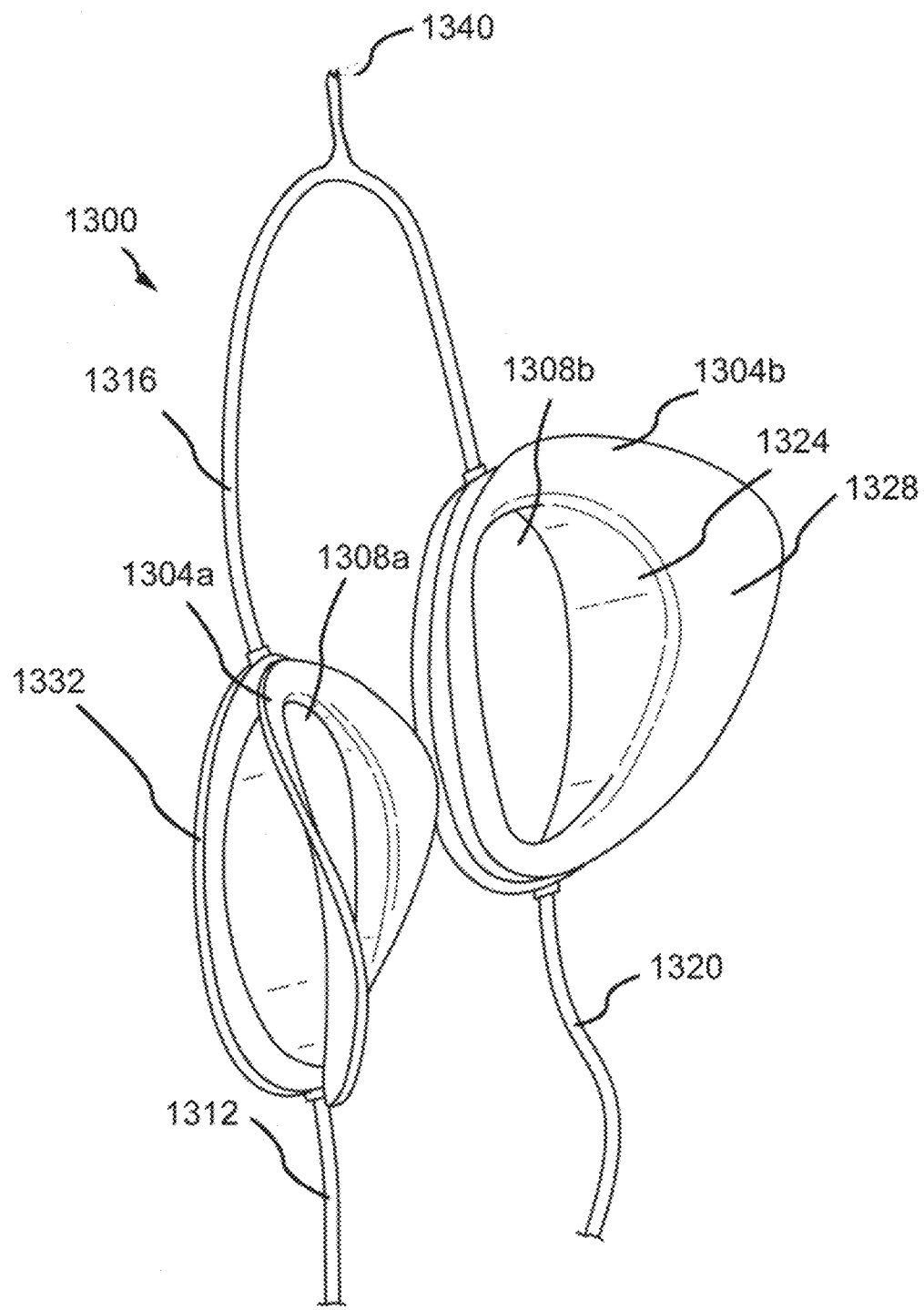
FIG. 13 is a rendering of eye imaging goggles for an ultrasound imaging system according to the present disclosure.

FIG. 13 is a rendering of imaging goggles 1300 for an ultrasound imaging system. The imaging goggles are shown attached to an ultrasound imaging system with a patient in position for scanning in FIGS. 12 and 14. These imaging goggles replace the Insight 100™ eye piece. The imaging goggles are constructed using the materials and assembly techniques used in the eye piece design of the Insight 100™. The imaging goggles enable better coupling between the patient and the instrument and can allow both eyes of the patient to be scanned without the patient moving.

With continuing reference to FIG. 13, the disposable imaging goggles comprise left and right eye pieces 1304a and 1304b having a water impermeable membrane 1308a and 1308b positioned in the viewing area of each eye piece to cause water to be maintained in contact with the patent's eye during imaging to provide an optically transparent and continuous acoustic transmission path for ultrasound energy. The saline water flows from the saline reservoir, through one or more input ports in each of the eye pieces 1308a and 1308b into a sealed volume defined by the membrane 1308a and 1308b, the interior walls 1324 and 1328 of each eye piece and the patient's left eye and surrounding eye socket. Saline can be drained, when scanning is completed, from either eye piece 1304a and 1308b through a tube 1312 and 1320, respectively, to a saline catch bin.

The materials and construction of the imaging goggles are based on similar materials and construction techniques developed for the Insight 100™ eye piece described in FIG. 7. The ridge 1332 on the front plastic frames of each eye piece of the imaging goggles slides into a corresponding matching slot on a mounting ring for each eye piece on the ultrasound imaging system 1200. This design allows a patient to engage with the instrument and be in position to 1) have one eye scanned by ultrasound while the other is imaged optically to follow eye motion during scanning and 2) allow the ultrasound and optical scans to be reversed so that both eyes can be scanned without the patient having to move.

When attached to the patient and the instrument, the imaging goggles contain the saline solution that completes the acoustic path from the patient's eye to the water in the interior of the instrument in which the scan head and positioner are immersed. The imaging goggles also separate the distilled water in which the scan head mechanism is immersed from the saline solution in which the patient's eyes are immersed.

The imaging goggles serve to complete a continuous (substantially constant acoustic impedance) acoustic path for ultrasonic scanning, that path extending from the transducer to the surface of the patient's eye. As noted above, the goggle membranes are also optically transparent.

FIG. 14 is another rendering for an ultrasound imaging system with a patient in position to be scanned, according to the present disclosure. As can be seen, the slanted styling of the front face of the instrument allows any saline leakage from the imaging goggles to drip into a saline catchment tray 1405 or saline catch bin located on the bottom front of the instrument. This figure illustrates the location of the distilled water reservoir 1407 and its circulation system; and the electronics housing. The control and image processing computer and memory are now on a circuit board situated within the electronics section 1406 of the desktop device which is internal to the instrument housing. The electronics housing which contains the system computer board has easy access compared to that of the Insight 100™.

FIG. 15 is another rendering of an ultrasound imaging system 1500 showing additional elements of the system. The imaging goggles 1510 described in FIG. 13 are shown attached to the instrument. The ridges 1506 on the front plastic frames of the imaging goggles slide into a matching slots on the ultrasound imaging system 1500. This figure shows the section of the instrument housing 1508 that contains the scan head 1509. There is also a compartment in the top of the instrument in which as saline bag is inserted. There is a heating plate in the bottom of the compartment that warms the saline prior to introducing the saline into the imaging goggles after the patient is in place for scanning. The body temperature saline avoids the discomfort of introducing cold saline onto the patient's eyes. Alternatively, infrared heating lamps can be used to heat the saline as well.

A moveable monitor 1504 is also shown. The monitor 1504 receives status and imaging information from the ultrasound imaging system instrument 1500 by short range wireless communications.

Figure 16:
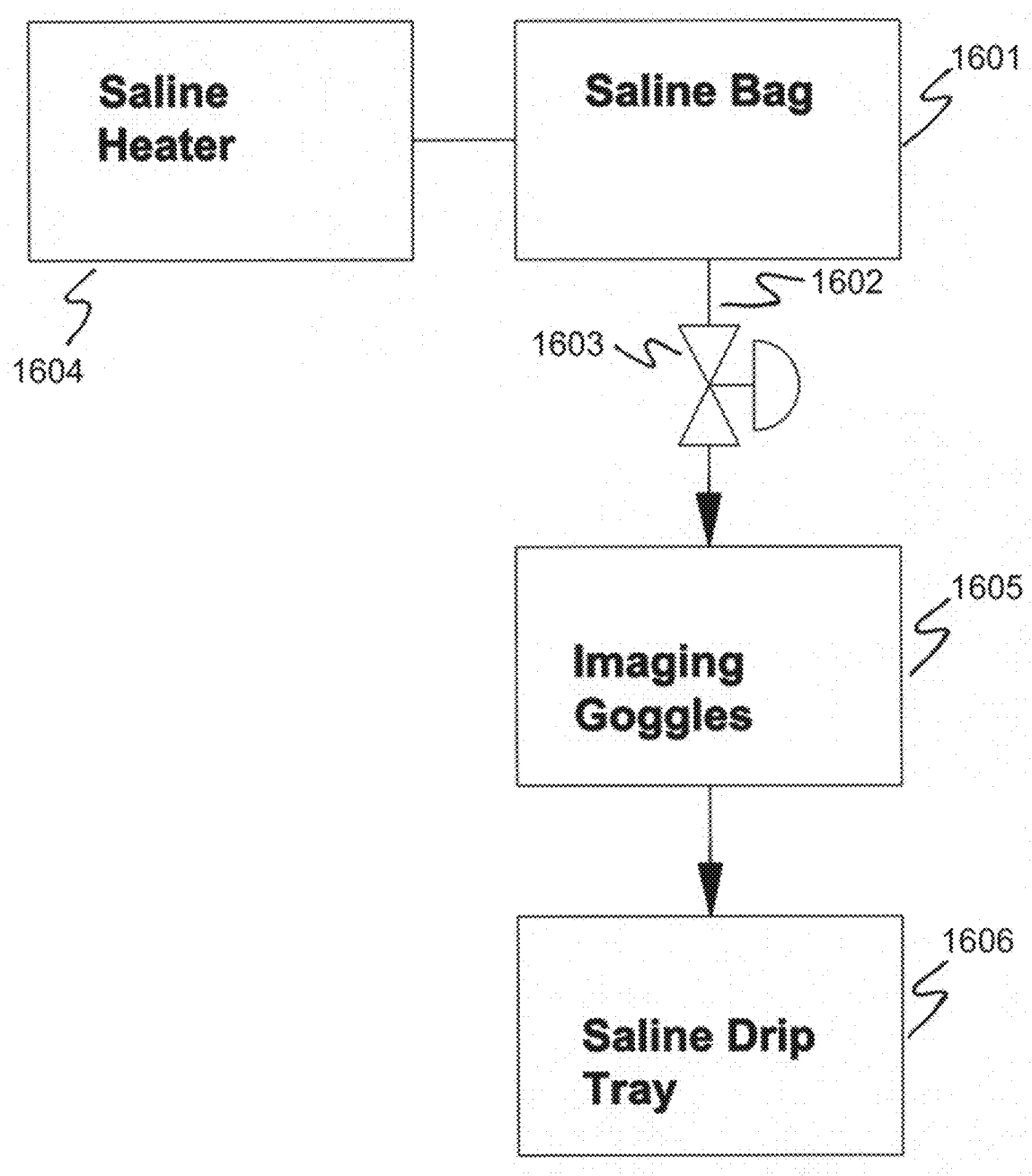
FIG. 16 illustrates the saline flow path for the imaging goggles.

FIG. 16 illustrates the saline flow path for the imaging goggles. A bag containing the saline solution 1601 is located inside the compartment in the top of the device such that the saline bag is above the scan patient's head. Alternatively a controlled weight or pump can be used to create the pressure to create sufficient flow. A flow tube 1602 connects the saline bag 1601 to the imaging goggles 1605. A hand operated or electronically controlled valve 1603 is used to open the flow tube 1602 to fill the imaging goggles 1605 with saline solution. When scanning is done the saline can be drained into the saline drip tray through drain tubes which can be manually or automatically be opened or closed. Saline leakage from the imaging goggles 1605 flows to a saline drip tray 1606 (also called a saline catch bin). As can be seen in FIG. 14, the Insight 200 instrument front face is sloped so that any saline leakage from the imaging goggles 1605 flows into the saline drip tray 1606.

Figure 17:
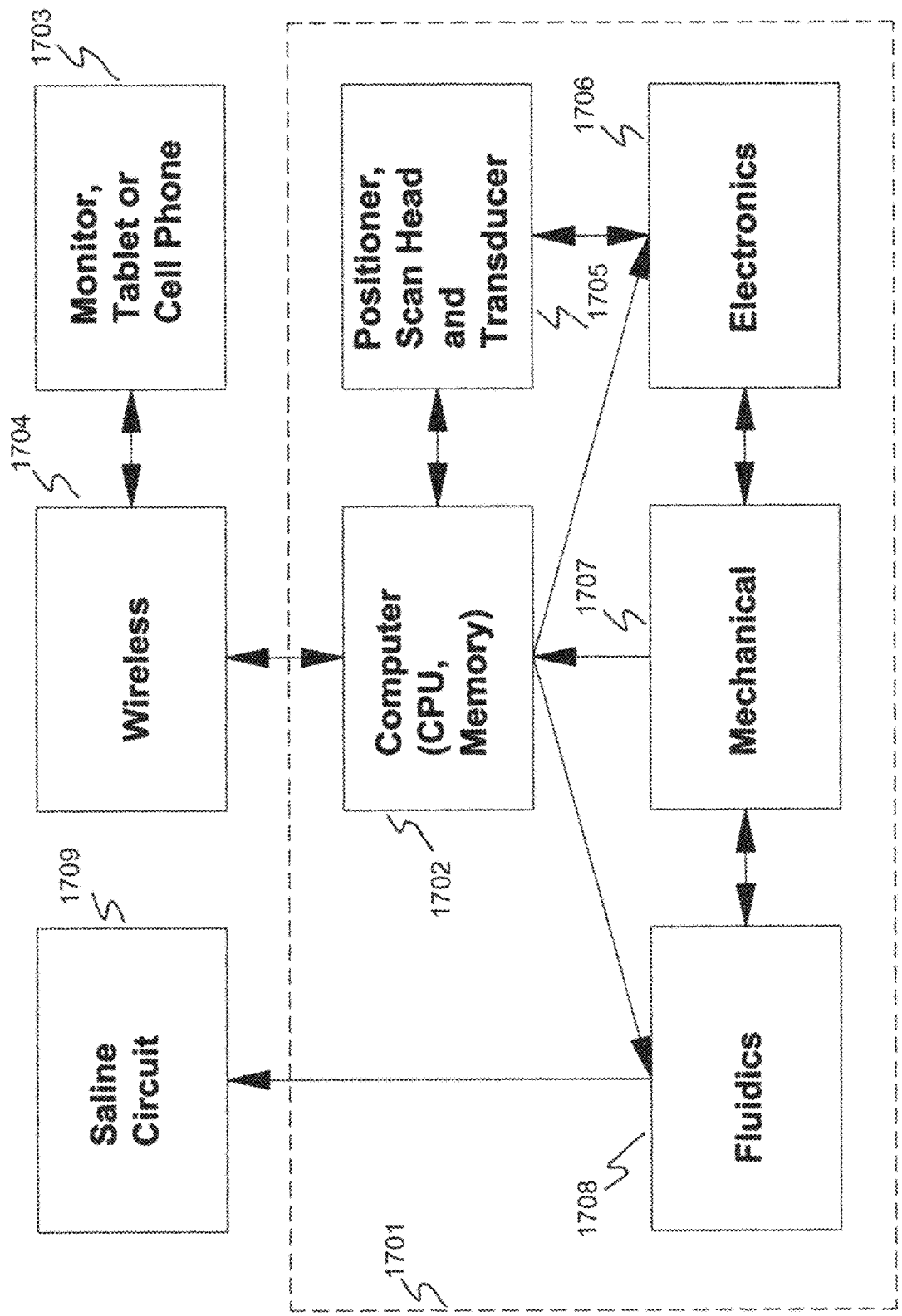
FIG. 17 illustrates the main functional elements of the Insight 200 ultrasonic imaging system.

FIG. 17 illustrates the main functional elements of the Insight 200 ultrasonic imaging system. An operator interacts with the main Insight 200 instrument body 1701 using a computer monitor, a tablet or a cell phone 1703 that communicates to the instrument computer 1702 via a wireless connection 1704. The computer 1702 is comprised of a CPU and internal memory and is located on a circuit board situated within the electronics section which, in turn, is located inside instrument body 1701.

An ultrasonic transducer is mounted on a carriage which is moved along an arcuate track which in turns is moved along a linear track (see FIG. 3 for example) during scanning. The arcuate track and linear track form the scan head which, in turn is mounted on a positioner mechanism as shown in FIG. 2, for example. The positioner, scan head and transducer 1705 provide transducer position data to the computer 1702 so that the computer 1702 can prescribe the appropriate positioner and scan head motions to generate the desired scan.

The fluidics module 1708 includes the filling and draining of the distilled water that fills instrument body 1701 and in which the positioner, scan head and transducer 1705 move. The fluidics module 1708 also includes a saline fluid circuit 1709 which fills and drains the saline fluid in the imaging goggles as described in FIG. 16.

The mechanics module 1707 includes the motors and belts that drive the positioner and linear track motors. Movement of the transducer carriage along the arcuate guide track is controlled by a series of embedded electromagnetic coils. The motion of the transducer carriage along the arcuate track and the motion of the arcuate track along the linear track are detected by a location sensing device which includes a position encoder mounted on the carriage. The encoder senses a position of the carriage by reading a series of magnetic strips along the length of the arcuate track and linear tracks. The aforementioned position encoder system is described in U.S. Pat. No. 8,758,252 "Innovative Components for an Ultrasonic Arc Scanning Apparatus" which is incorporated herein by reference.

The electronics module 1708 includes the ultrasound pulser and receiver circuit board and the A/D circuit board. The typical firing rate of the ultrasound pulser is about 1 pulse every 250 microseconds. A 16 bit A/D board samples at about 250 million samples per second (about a sample every 4 nanoseconds). A Model 277 Quad 16-bit/250 MHz ADC Digitizer from Red Rapids in Plano Texas is an example of such a commercially available A/D board.

The sensor array comprises linear or angular position sensors that, among other things, track the relative and/or absolute positions of the various movable components and the alignment of various stationary and moveable components, such as, but not limited to, the one or more position tracking sensors, the positioning arms and probe carriage assembly, the fixation lights, the optical video camera, the arcuate guide assembly, the ultrasound transducer probe, the probe carriage, the linear guide track, the motors to move the position arms, motors to move the arcuate guide assembly, and motors to move the probe carriage. The sensor array may comprise any suitable type of positional sensors, including inductive non-contact position sensors, string potentiometers, linear variable differential transformers, potentiometers, capacitive transducers, eddy-current sensors, Hall effect sensors, proximity sensors (optical), grating sensors, optical encoders (rotary or linear), and photodiode arrays. Candidate sensor types are discussed in U.S. Pat. No. 8,758,252.

The controlled device is any device having an operation or feature controlled by a computer. Controlled devices include the various movable or activatable components, such as, but not limited to, the one or more position tracking sensors, the positioning arms and the transducer carriage assembly, the fixation lights, the optical video camera, the arcuate guide assembly, the ultrasound transducer probes and the probe carriage, the linear guide track, the motors to move the position arms, motors to move the arcuate guide assembly, and motors to move the probe carriage.

The computer may comprise a software-controlled device that includes, in memory, a number of modules executable by a processor. The executable modules include a controller to receive and process positioning signals from the sensor array and generate and transmit appropriate commands to the monitored controlled device, an imaging module to receive and process A- and B-scan images to produce two-, three-, or four-dimensional images of selected ocular components or features, and a measurement module 2040 to determine, as discussed above, the dimensions and/or volumes of selected ocular components and/or features. The imaging algorithm used by the imaging module is further discussed U.S. Pat. No. 8,496,588.

In one embodiment, the controller determines an adjustment to the position of the transducer based on receiving a control measurement input from the sensor array. In another embodiment, the controller provides a control input to the drive mechanism of the probe carriage, the positioning arm, the arcuate guide assembly, and/or the linear guide track. In yet another embodiment, the controller provides a control input to comprise controlling the power, frequency, signal/noise ratio, pulse rate, gain schedule, saturation thresholds, and sensitivity of the optical and/or ultrasound transducers. In still another embodiment, the controller utilizes control algorithms comprising at least one of on/off control, proportional control, differential control, integral control, state estimation, adaptive control and stochastic signal processing. Controller may also monitor and determine if any faults or diagnostic flags have been identified in one or more elements, such as the optical and/or ultrasound transducers and/or carriage.

In yet another embodiment, the disclosed systems and methods may be partially implemented in software that can be stored on a storage medium to include a computer-readable medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

In one embodiment, one or more computers are used to control, among other things, the combined UHFU and OCT imaging system, the scan head assembly, the OCT sample arm probe, OCT reference arm, and/or the ultrasound transducer and/or the position sensor(s). In one embodiment, the user interacts with the computer through any means known to those skilled in the art, to include a keyboard and/or display to include a touch-screen display. The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

A number of variations and modifications of the disclosure can be used. As will be appreciated, it would be possible to provide for some features of the disclosure without providing others.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover though the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A method comprising:
    imaging, by an ultrasound transducer of an ultrasound imaging system, an ocular structure of a first eye of a patient, wherein a fixation light is viewable by a second eye of the patient, but not the first eye during imaging; and
    imaging, by the ultrasound transducer, an ocular structure of the second eye of the patient, wherein the fixation light is viewable by the first eye, but not the second eye, of the patient during imaging,
    wherein the first eye and the second eye are imaged.

2. The method of claim 1, wherein, while imaging the ocular structure of the first eye, a visual field of the first eye is maintained in darkness and, while imaging the ocular structure of the second eye, a visual field of the second eye is maintained in darkness.

3. The method of claim 2, wherein no viewable object is provided in the visual field of the eye being imaged.

4. The method of claim 1, further comprising:
    providing an enclosure on a support surface, the enclosure having a window portion positioned in a side wall of the enclosure, wherein the window portion is substantially acoustically and optically transparent, and the enclosure is filled with a first fluid to a level above the window portion;
    providing imaging goggles wherein the goggle lenses are substantially acoustically and optically transparent and a second fluid is disposed in the volume of the imaging goggles between an interior surface of the imaging goggles and the eye of the patient;
    providing an ultrasound transducer imaging system in the first fluid, the ultrasound transducer imaging system having an ultrasound transducer operably interconnected to an arcuate track;
    positioning the patient wearing the imaging goggles at the window portion of the enclosure with the imaging goggles being engaged with a border of the window portion;
    scanning the first and second eyes of the patent using the ultrasound transducer imaging system, wherein the ultrasound transducer records first and second sets of A-scan images of the first and second eyes of the patient, respectively; and
    combining, by a computer, a plurality of A-scan images in the first set to form a B-scan image of the first eye and a plurality of A-scan images in the second set to form a B-scan image of the second eye, wherein a radius of curvature of the arcuate guide track is no more than about 95 mm.

5. The method of claim 1, wherein the eyes of the patient are maintained in a fixed location relative to an arcuate guide track of the ultrasound imaging system during imaging by imaging goggles.

6. The method of claim 5, wherein the imaging goggles comprises one of a ridge and slot that is received by the other of the one of the ridge and slot of an instrument.

7. The method of claim 5, wherein a center of curvature of the arcuate guide track is positioned between a posterior surface of a lens and a cornea of the eye of the patient.

8. The method of claim 5, wherein the ultrasound imaging system includes a carriage movable along the arcuate guide track.

9. The method of claim 8, wherein the imaging goggles and ultrasound transducer are positioned relative to each other such that, at a plurality of positions of the carriage along the arcuate guide track, a focal plane of the ultrasound transducer is positioned inside of an anterior segment of the eye.

10. The method of claim 1, wherein, while imaging the ocular structure of the first eye, a visual image is also viewable by the second eye and, while imaging the ocular structure of the second eye, the visual image is also viewable by the first eye.

11. An ultrasound imaging method comprising:
    generating, by an ultrasound imaging system, a first image of a first eye of a patient, a fixation light being viewable by a second eye of the patient, but not the first eye during the generation of the first image; and
    thereafter, generating, by the ultrasound imaging system, a different second image of the second eye of the patient, the fixation light being viewable by the first eye, but not the second eye, of the patient during generation of the second image,
    wherein the first eye and the second eye are imaged.

12. The method of claim 11, further comprising:
    providing an enclosure on a support surface, the enclosure having a window portion positioned in a side wall of the enclosure, wherein the window portion is substantially acoustically and optically transparent, and the enclosure is filled with a first fluid to a level above the window portion;
    providing imaging goggles with goggle lenses, wherein the goggle lenses are substantially acoustically and optically transparent and a second fluid is disposed in a volume of the imaging goggles between an interior surface of the imaging goggles and the eye of the patient;
    providing an ultrasound transducer imaging system in the first fluid, the ultrasound transducer imaging system having an ultrasound transducer operably interconnected to an arcuate track;
    positioning the patient wearing the imaging goggles at the window portion of the enclosure with the imaging goggles being engaged with a border of the window portion;
    scanning the first and second eyes of the patent using the ultrasound transducer imaging system, wherein the ultrasound transducer records first and second sets of A-scan images of the first and second eyes of the patient, respectively; and combining, by a computer, a plurality of A-scan images in the first set to form a B-scan image of the first eye and a plurality of A-scan images in the second set to form a B-scan image of the second eye, wherein a radius of curvature of the arcuate guide track is no more than about 95 mm.

13. The method of claim 11, wherein, while the first image is generated, a visual field of the first eye is maintained in darkness and, while the second image is generated, a visual field of the second eye is maintained in darkness.

14. The ultrasound imaging system of claim 11, wherein no viewable object is provided in a visual field of the eye being imaged.

15. The method of claim 11, wherein the eyes of the patient are maintained in a fixed location relative to an arcuate guide track of the ultrasound imaging system during imaging by imaging goggles.

16. The method of claim 15, wherein the imaging goggles comprises one of a ridge and slot that is received by the other of the one of the ridge and slot of the instrument.

17. The method of claim 15, wherein a center of curvature of the arcuate guide track is positioned between a posterior surface of a lens and a cornea of the eye of the patient.

18. The method of claim 15, wherein the ultrasound imaging system includes a carriage movable along the arcuate guide track.

19. The method of claim 18, wherein the imaging goggles and ultrasound transducer are positioned relative to each other such that, at a plurality of positions of the carriage along the arcuate guide track, a focal plane of the ultrasound transducer is positioned inside of an anterior segment of the eye.

20. A method comprising:

imaging, by an ultrasound transducer of an ultrasound imaging system, an ocular structure of a first eye of a patient, wherein a fixation light is viewable by a second eye of the patient, but not the first eye during imaging, and wherein a visual field of the first eye is maintained in darkness; and imaging, by the ultrasound transducer, an ocular structure of the second eye of the patient, wherein the fixation light is viewable by the first eye, but not the second eye, of the patient during imaging, and wherein a visual field of the second eye is maintained in darkness, wherein the first eye and the second eye are imaged.

* * * * *